(12) United States Patent
Shroff et al.

(10) Patent No.: US 6,914,069 B2
(45) Date of Patent: Jul. 5, 2005

(54) PHARMACEUTICALLY ACTIVE COMPOUNDS AND METHODS OF USE

(75) Inventors: Hitesh Shroff, Bedford, MA (US); Adulla P. Reddy, Norwood, MA (US); Nabil El Tayar, deceased, late of Milton, MA (US); by Susan A. Kiernan, legal representative, Curacao (AN); Nadia Brugger, Boston, MA (US); Catherine Jorand-Lebrun, Boston, MA (US)

(73) Assignee: Applied Research Systems ARS Holding N.V., Netherland (AN)

( * ) Notice: Subject to any disclaimer, the term of this patent is extended or adjusted under 35 U.S.C. 154(b) by 78 days.

(21) Appl. No.: 09/860,658

(22) Filed: May 19, 2001

(65) Prior Publication Data

US 2002/0132844 A1 Sep. 19, 2002

Related U.S. Application Data

(60) Provisional application No. 60/205,814, filed on May 19, 2000.

(51) Int. Cl.$^7$ ..................... A61K 31/44; C07D 401/00
(52) U.S. Cl. ..................................... 514/341; 546/275.4
(58) Field of Search ....................... 514/341; 546/275.4

(56) References Cited

U.S. PATENT DOCUMENTS

| | | | |
|---|---|---|---|
| 3,842,088 A | 10/1974 | Habeck et al. .............. 260/296 |
| 4,833,135 A | 5/1989 | Edwards et al. ............. 514/212 |
| 5,017,557 A | 5/1991 | Fabbri et al. .................. 514/12 |
| 5,486,618 A | 1/1996 | Hagen et al. ............. 548/362.1 |
| 5,639,639 A | 6/1997 | Reddy et al. .............. 435/69.4 |
| 5,744,493 A | 4/1998 | Boigegrain et al. ......... 514/359 |
| 5,767,067 A | 6/1998 | Arpaia et al. ................... 514/8 |
| 5,986,104 A | 11/1999 | Hamper et al. .......... 548/377.1 |
| 6,191,147 B1 | 2/2001 | Brown et al. ............... 514/339 |

FOREIGN PATENT DOCUMENTS

| WO | WO 97/12884 | 4/1997 |
|---|---|---|
| WO | WO 98/15532 | 4/1998 |
| WO | WO 98/22101 | 5/1998 |

OTHER PUBLICATIONS

Kelton et al., *Molecular and Cellular Endocrinology*, vol. 89, pp. 141–151, 1992.
Marzinzik et al., *Tetrahedron Letters*, vol. 37, No. 7: 1003–1006; 1996.
Marzinzik et al., *J. Org. Chem.*, vol. 63, pp. 723–727, 1998.
Murray, *Tetrahedron Letters*, vol. 34, No. 12, p. 1863–1866, 1993.
Stauffer et al., *Bioorganic and Medicinal Chemistry*, vol. 9, pp. 141–150; 2001.
Fray et al., *J. Chem. Research*, vol. (S), p. 11; 1992.

*Primary Examiner*—Deborah C. Lambkin
(74) *Attorney, Agent, or Firm*—Peter F. Corless; Christine C. O'Day; Edwards & Angell, LLP

(57) ABSTRACT

The invention provides substituted pyrazole compounds, and methods of treatment and pharmaceutical compositions that utilize or comprise one or more such compounds. Compounds of the invention are useful for the treatment of mammalian infertility.

19 Claims, No Drawings

PHARMACEUTICALLY ACTIVE COMPOUNDS AND METHODS OF USE

The present application claims the benefit of U.S. provisional application No. 60/205,814, filed May 19, 2000, incorporated herein by reference in its entirety.

BACKGROUND OF THE INVENTION

1. Field of the Invention

The present invention relates to substituted pyrazole compounds, and methods of treatment and pharmaceutical compositions that utilize or comprise one or more such compounds. Compounds of the invention are useful for the treatment of mammalian infertility.

2. Background

Luteinizing Hormone (LH) and Follicle Stimulating Hormone (FSH) are produced by the anterior pituitary gland and are involved in mammalian reproductive processes. The glycoprotein family of pituitary hormones such as FSH, LH and the thyropropic hormone (TSH) contain carbohydrate moieties and have common α-subunit and distinct β-subunits (1–4) providing receptor recognition and specificity. These proteins are relatively large (28–38 kDa) heterodimeric glycoproteins.

LH is released from the anterior pituitary gland under the influence of gonadotropin releasing hormone and progesterones. In the female LH stimulates ovulation and is the major hormone involved in the regulation of progesterone secretion by the corpus luteum. In the male LH stimulates Leydig cells to secrete andogens, particularly testosterone.

FSH is released from the anterior pituary under the influence of gonadotropin releasing hormone, oestrogens and from the placenta during pregnancy. FSH acts on the ovaries stimulating maturation of follicles and regulates secretion of oestrogens. In the male FSH is responsible for the integrity of the seminiferous tubules and acts on Sertoli cells to support gametogenesis.

The LH and FSH receptors belong to the family of G protein coupled receptors, which are complex transmembrane proteins characterized by seven hydrophobic helices. LH and FSH receptors also share close sequence homology (approximately 40%). The receptors' extracellular domains bind to their respective hormones with high affinity and specificity. The intracellular portion of FSH and LH receptors is coupled to a Gs protein. Upon receptor activation, the hormonal interaction with the extracellular domain results in a cascade of events that lead to specific biological effects of the gonadotropin.

LH and FSH have been used for treatment for female infertility and spermatogenesis disorders. See U.S. Pat. Nos. 5,767,067; 5,639,639; and 5,017,557.

However, those therapies have some notable shortcomings. For instance, current FSH treatment is limited by lack of oral bioavailability, high costs and need of close medical personnel supervision throughout an administration protocol.

It thus would be desirable to have new agents and methods to treat infertility in mammals.

SUMMARY OF THE INVENTION

We have now found that substituted pyrazole compounds are potent Luteinizing Hormone (LH) and Follicle Stimulating Hormone (FSH) agonists. Compounds of the invention are particularly useful for treatment of infertility in mammals.

Pyrazole compounds of the invention are substituted by other than hydrogen in one or more pyrazole ring positions, and preferably are substituted at the 1, 3, 4 and/or 5 ring positions by a non-hydrogen substituent. Typical pyrazole compounds of the invention are substituted at least at the 5-ring position by other than hydrogen.

Generally preferred for use in the therapeutic methods of the invention are substituted pyrazole compounds of the following Formula I:

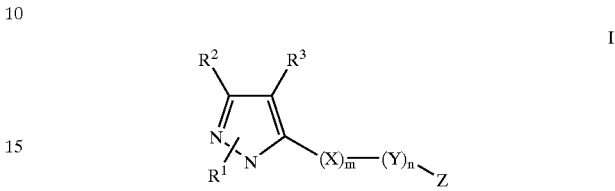

wherein $R^1$ is hydrogen; optionally substituted alkyl preferably having 1 to about 20 carbons, more preferably 1 to about 12 carbons; optionally substituted alkenyl preferably having 2 to about 20 carbon atoms, more preferably 2 to about 12 carbon atoms; optionally substituted alkynyl preferably having 2 to about 20 carbon atoms, more preferably 2 to about 12 carbon atoms; optionally substituted carbocyclic aryl having at least about 6 ring carbon atoms; optionally substituted aralkyl having at least about 6 ring carbon atoms; optionally substituted heteroaromatic or heteroalicyclic group having 1 to 3 rings, 3 to 8 ring, members in each ring and from 1 to 3 hetero atoms (N, O or S); or optionally substituted heteroaralkyl or heteroalicyclicalkyl group having from 1 to 3 rings, 3 to 8 ring members in each ring and from 1 to 3 hetero atoms (N, O or S);

$R^2$ and $R^3$ are each independently hydrogen, halogen, optionally substituted alkyl preferably having 1 to about 20 carbons, more preferably 1 to about 12 carbons; optionally substituted alkenyl preferably having 2 to about 20 carbon atoms, more preferably 2 to about 12 carbon atoms; optionally substituted alkynyl preferably having 2 to about 20 carbon atoms, more preferably 2 to about 12 carbon atoms; optionally substituted alkoxy preferably having from 1 to about 20 carbon atoms, more preferably 1 to about 12 carbon atoms; optionally substituted alkylthio preferably having from 1 to about 20 carbon atoms, more preferably 1 to about 12 carbon atoms; optionally substituted alkylsulfinyl preferably having from 1 to about 20 carbon atoms, more preferably 1 to about 12 carbon atoms; optionally substituted alkylsulfonyl preferably having from 1 to about 20 carbon atoms, more preferably 1 to about 12 carbon atoms; optionally substituted carbocyclic aryl having at least about 6 ring carbon atoms; optionally substituted aralkyl having at least about 6 ring carbon atoms; optionally substituted heteroaromatic or heteroalicyclic group having from 1 to 3 rings, 3 to 8 ring members in each ring and from 1 to 3 hetero atoms (particularly 1–3 N, O and/or S atoms); or optionally substituted heteroaralkyl or heteroalicyclicalkyl group having from 1 to 3 rings, 3 to 8 ring members in each ring and from 1 to 3 hetero atoms (particularly 1–3 N, O and/or S atoms);

wherein preferably at least one of $R^1$, $R^2$ and $R^3$ are other than hydrogen and more preferably at least two of $R^1$, $R^2$ and $R^3$ are other than hydrogen;

X is optionally substituted alkylene preferably having 1 to about 12 chain carbons, more preferably 2 to about 8 chain carbons, still more preferably 3 to about 6 alkylene chain carbons; optionally substituted alkenylene preferably having 2 to about 12 chain carbons, more preferably 2 to about 8 chain carbons, still more preferably 3 to about 6 alkenylene chain carbons; optionally substituted alkynylene preferably having 2 to about 12 chain carbons, more preferably 2 to about 8 chain carbons, still more preferably 3 to about 6 alkynylene chain carbons; optionally substituted heteroalkylene preferably having 1 to about 12 chain carbons, more preferably 2 to about 8 chain carbons, still more preferably 3 to about 6 heteroalkylene chain carbons and a total of 4 or 5 atoms in the heteroalkylene chain inclusive of hetero atoms (particularly N, O and/or S atoms); optionally substituted heteroalkenylene preferably having 2 to about 12 chain carbons, more preferably 2 to about 8 chain carbons, still more preferably 3 to about 6 heteroalkenylene chain carbons and a total of 4 or 5 atoms in the heteroalkenylene chain (particularly N, O and/or S atoms); optionally substituted heteroalkynynylene preferably having 2 to about 12 chain carbons, more preferably 2 to about 8 chain carbons, still more preferably 4 or 5 heteroalkynylene chain carbons and a total of 4 or 5 atoms in the heteroalkynylene chain inclusive of hetero atoms (particularly N, O and/or S atoms); or X is optionally alicyclic, optionally substituted carbocyclic aryl; optionally substituted heteroalicyclic, optionally substituted heteroaromatic, optionally substituted heteroaralkyl, or optionally substituted heteroalicyclicalkyl group, each preferably having 3–10 carbon or hetero atoms in a ring, more preferably 5 or 6 membered ring(s), and 1–3 N, O or S atoms;

Y is optionally substituted amino; optionally substituted methylene (e.g. unsubstituted methylene, $CH_2$), carbonyl ($C=O$); or sulfonyl ($SO_2$);

Z is an optionally substituted alkylamine; an amino acid (natural or non-natural amino acid) including a β-amino acid; or a glycine; or a derivative thereof, attached to the rest of the molecule either by its amino or carboxylic acid residue depending on the nature of Y; m is 0 (where no X group is present) or 1, and preferably m is 1; n is 0 (where no Y group is present) or 1, and preferably n is 1; and pharmaceutically acceptable salts thereof.

Preferred compounds of Formula I include those of the following Formula I':

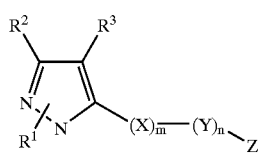

wherein $R^1$, $R^2$ and $R^3$ are each independently hydrogen; optionally substituted alkyl preferably having 1 to about 20 carbons, more preferably 1 to about 12 carbons; optionally substituted alkenyl preferably having 2 to about 20 carbon atoms, more preferably 2 to about 12 carbon atoms; optionally substituted alkynyl preferably having 2 to about 20 carbon atoms, more preferably 2 to about 12 carbon atoms; optionally substituted alkoxy preferably having 1 to about 20 carbon atoms, more preferably 1 to about 12 carbon atoms; optionally substituted alkylthio preferably having 1 to about 20 carbon atoms, more preferably 1 to about 12 carbon atoms; optionally substituted alkylsulfinyl preferably having 1 to about 20 carbon atoms, more preferably 1 to about 12 carbon atoms; optionally substituted alkylsulfonyl preferably having 1 to about 20 carbon atoms, more preferably 1 to about 12 carbon atoms; optionally substituted carbocyclic aryl having at least 6 ring carbon atoms; optionally substituted aralkyl having at least 6 ring atoms; optionally substituted heteroaromatic or heteroalicyclic group having 1 to 3 rings, 3 to 8 ring members in each ring and from 1 to 3 hetero atoms (N, O or S); or optionally substituted heteroaralkyl or heteroalicyclicalkyl having 1 to 3 rings, 3 to 8 ring members in each ring and from 1 to 3 hetero atoms (particularly N, O or S);

X is optionally substituted alkylene preferably having 1 to about 12 chain carbons, more preferably 2 to about 8 chain carbons, still more preferably 3 to about 6 alkylene chain carbons; optionally substituted alkenylene preferably having 2 to about 12 chain carbons, more preferably 2 to about 8 chain carbons, still more preferably 3 to about 6 alkenylene chain carbons; optionally substituted alkynylene preferably having 2 to about 12 chain carbons, more preferably 2 to about 8 chain carbons, still more preferably 3 to about 6 alkynylene chain carbons; optionally substituted heteroalkylene preferably having 1 to about 12 chain carbons, more preferably 1 to about 8 chain carbons, still more preferably 3 to about 6 heteroalknylene chain carbons and a total of 4 or 5 atoms in the heteroalkylene chain (inclusive of N, O or S atoms); optionally substituted heteroalkenylene preferably having 2 to about 12 chain carbons, more preferably 2 to about 8 chain carbons, still more preferably 3 to about 6 heteroalkenylene chain carbons and a total of 4 or 5 atoms in the heteroalkenylene chain (inclusive of N, O or S atoms); optionally substituted heteroalkynynylene preferably having 2 to about 12 chain carbons, more preferably 2 to about 8 chain carbons, still more preferably 3 to about 6 heteroalkynylene chain carbons and a total of 4 or 5 atoms in the heteroalkynylene chain (inclusive of N, O or S atoms);

or X is optionally substituted alicyclic; optionally substituted carbocyclic aryl; optionally substituted aralkyl; optionally substituted heteroaromatic; optionally substituted heteroalicyclic group; optionally substituted heteroaralkyl; or optionally substituted heteroalicyclicalkyl group, each preferably having 3 to 10 carbon or hetero (N, O or S) atoms in a ring, more preferably 5 or 6 membered ring(s), and 1–3 N, O or S atoms;

Y is optionally substituted amino; optionally substituted methylene; carbonyl; or sulfonyl;

Z is an optionally substituted alkylamine; an amino acid (natural or non-natural amino acid) including a β-amino acid; or a glycine; m is 0 (where no X group is present) or 1, and preferably m is 1; n is 0 (where no Y group is present) or 1, and preferably n is 1; and pharmaceutically acceptable salts thereof.

Preferred compounds of Formula I also include those where the pyrazole ring nitrogen has a non-hydrogen substituent, such as compounds of the following Formula IA:

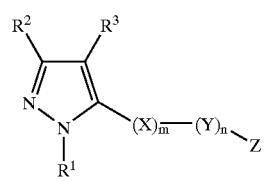

wherein $R^1$ is a non-hydrogen substituent selected from the same group as defined for $R^1$ in Formula I above; $R^2$, $R^3$, X, Y, Z, m and n are the same as defined in Formula I above; and pharmaceutically acceptable salts thereof.

Preferred R¹ groups of compounds of Formula IA include optionally substituted alkyl; optionally substituted alkenyl; optionally substituted carbocyclic aryl; optionally substituted aralkyl; optionally substituted heteroaromatic; optionally substituted heteroalicyclic group; optionally substituted heteroarylakyl; or optionally substituted heteroalicyclicalkyl group.

Preferred compounds of the invention also include those having a non-hydrogen substituent at the pyrazole 1- and 3-positions, such as compounds of the following Formula IB:

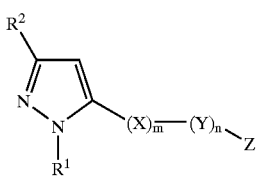

IB wherein R¹ and R² are each non-hydrogen substituents independently selected from the same group as defined for R¹ and R² in Formula I above; X, Y, Z, m and n are the same as defined in Formula I above; and pharmaceutically acceptable salts thereof.

Preferred R¹ groups of compounds of Formula IB include optionally substituted alkyl; optionally substituted alkenyl; optionally substituted carbocyclic aryl; optionally substituted aralkyl; optionally substituted heteroaromatic; optionally substituted heteroalicyclic group; optionally substituted heteroarylakyl; or optionally substituted heteroalicyclicalkyl group.

Preferred compounds of the invention also include those having a non-hydrogen substituent at the pyrazole 1- and 3-positions, such as compounds of the following Formula IC:

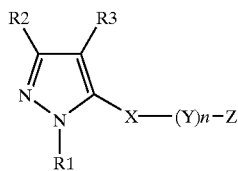

IC wherein R¹ and R² are each non-hydrogen substituents independently selected from the same group as defined in Formula I above;

R³, Y, Z, and n are the same as defined in Formula I above;

X is optionally substituted heteroalkylene preferably having 1 to about 12 chain carbons, more preferably 2 to about 8 chain carbons, still more preferably 3 to about 6 heteroalkylene chain carbons and a total of 4 or 5 atoms in the heteroalkylene chain inclusive of N, O and/or S atoms; optionally substituted heteroalkenylene preferably having 2 to about 12 chain carbons, more preferably 2 to about 8 chain carbons, still more preferably 3 to about 6 heteroalkenylene chain carbons and a total of 4 or 5 atoms in the heteroalkenylene chain inclusive of N, O or S atoms; optionally substituted heteroalkynynylene preferably having 2 to about 12 chain carbons, more preferably 2 to about 8 chain carbons, still more preferably 4 or 5 heteroalkynylene chain carbons and a total of 4 or 5 atoms in the heteroalkynylene chain inclusive of N, O or S atoms; and pharmaceutically acceptable salts thereof.

Preferred compounds of the invention also include those having a non-hydrogen substituent at the pyrazole 1- and 3-positions, such as compounds of the following Formula ID

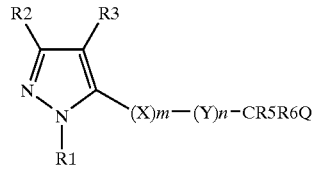

ID wherein R¹ and R² are each non-hydrogen substituents independently selected from the same group as defined in Formula I above;

R³, X, Y, m and n are the same as defined in Formula I above;

R⁵ and R⁶ are independently hydrogen, optionally substituted alkyl preferably having 1 to about 20 carbons, more preferably 1 to about 12 carbons; optionally substituted alkenyl preferably having 2 to about 20 carbon atoms, more preferably 2 to about 12 carbon atoms; optionally substituted alkynyl preferably having 2 to about 20 carbon atoms, more preferably 2 to about 12 carbon atoms; optionally substituted carbocyclic aryl having at least about 6 ring carbon atoms; optionally substituted aralkyl having at least about 6 ring carbon atoms; optionally substituted heteroaromatic or heteroalicyclic group having from 1 to 3 rings, 3 to 8 ring members in each ring and from 1 to 3 hetero atoms; or optionally substituted heteroaralkyl or heteroalicyclicalkyl group having from 1 to 3 rings, 3 to 8 ring members in each ring and from 1 to 3 hetero atoms more preferably one of R⁵ and R⁶ is hydrogen; and Q is omitted (it does not exist) or is —(CH₂)p-CO-A-R⁷ wherein p is 0, 1 or 2, A is O or NH and R⁷ is independently hydrogen, optionally substituted alkyl preferably having 1 to about 20 carbons, more preferably 1 to about 12 carbons; optionally substituted alkenyl preferably having 2 to about 20 carbon atoms, more preferably 2 to about 12 carbon atoms; optionally substituted alkynyl preferably having 2 to about 20 carbon atoms, more preferably 2 to about 12 carbon atoms; optionally substituted carbocyclic aryl having at least about 6 ring carbon atoms; optionally substituted aralkyl having at least about 6 ring carbon atoms; optionally substituted heteroaromatic or heteroalicyclic group 1 to 3 rings, 3 to 8 ring members in each ring and from 1 to 3 hetero atoms (particularly 1–3 N, O and/or S atoms); or optionally substituted heteroaralkyl or heteroalicyclicalkyl group having from 1 to 3 rings, 3 to 8 ring members in each ring and from 1 to 3 hetero atoms (particularly 1–3 N, O and/or S atoms); and pharmaceutically acceptable salts thereof.

Preferred compounds of the invention also include those having a non-hydrogen substituent at the pyrazole 1- and 3-positions, such as compounds of the following Formula IE

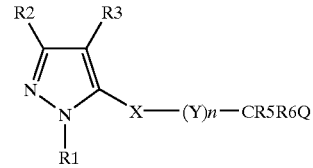

IE wherein R¹ and R² are each non-hydrogen substituents independently selected from the same group as defined in Formula I above; R³, Y and n are the same as defined in Formula I above; X is optionally substituted heteroalkylene preferably having 1 to about 12 chain carbons, more preferably 2 to about 8 chain carbons, still more preferably 3 to about 6 heteroalkylene chain carbons and a total of 4 or 5 atoms in the heteroalkylene chain inclusive of N, O and/or S atoms; optionally substituted heteroalkenylene preferably having 2 to about 12 chain carbons, more preferably 2 to about 8 chain carbons, still more preferably 3 to about 6 heteroalkenylene chain carbons and a total of 4 or 5 atoms in the heteroalkenylene chain inclusive of N, O and/or S atoms; optionally substituted heteroalkynynylene preferably having 2 to about 12 chain carbons, more preferably 2 to about 8 chain carbons, still more preferably 4 or 5 heteroalkynylene chain carbons and a total of 4 or 5 atoms in the heteroalkynylene chain inclusive of N, O and/or S atoms;

$R^5$ and $R^6$ are independently hydrogen, optionally substituted alkyl preferably having 1 to about 20 carbons, more preferably 1 to about 12 carbons; optionally substituted alkenyl preferably having 2 to about 20 carbon atoms, more preferably 2 to about 12 carbon atoms; optionally substituted alkynyl preferably having 2 to about 20 carbon atoms, more preferably 2 to about 12 carbon atoms; optionally substituted carbocyclic aryl having at least about 6 ring carbon atoms; optionally substituted aralkyl having at least about 6 ring carbon atoms; optionally substituted heteroaromatic or heteroalicyclic group 1 to 3 rings, 3 to 8 ring members in each ring and from 1 to 3 hetero atoms (particularly 1–3 N, O and/or S atoms); or optionally substituted heteroaralkyl or heteroalicyclicalkyl group having from 1 to 3 rings, 3 to 8 ring members in each ring and from 1 to 3 hetero atom (particularly 1–3 N, O and/or S atoms), more preferably one of $R^5$ and $R^6$ is hydrogen; and Q is omitted (i.e. it is not present) or is —(CH2)p-CO-A-$R^7$ wherein p is 0, 1 or 2; A is O or NH and $R^7$ is independently hydrogen, optionally substituted alkyl preferably having 1 to about 20 carbons, more preferably 1 to about 12 carbons; optionally substituted alkenyl preferably having 2 to about 20 carbon atoms, more preferably 2 to about 12 carbon atoms; optionally substituted alkynyl preferably having 2 to about 20 carbon atoms, more preferably 2 to about 12 carbon atoms; optionally substituted carbocyclic aryl having at least about 6 ring carbon atoms; optionally substituted aralkyl having at least about 6 ring carbon atoms; optionally substituted heteroaromatic or heteroalicyclic group 1 to 3 rings, 3 to 8 ring members in each ring and from 1 to 3 hetero atoms (particularly 1–3 N, O and/or S atoms); or optionally substituted heteroaralkyl or heteroalicyclicalkyl group having from 1 to 3 rings, 3 to 8 ring members in each ring and from 1 to 3 hetero atoms (particularly 1–3 N, O and/or S atoms); and pharmaceutically acceptable salts thereof.

Preferred compounds of the invention also include those having a non-hydrogen substituent at the pyrazole 1- and 3-positions, such as compounds of the following Formula IF:

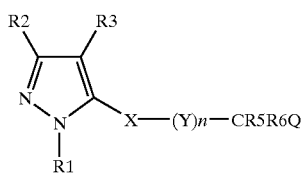

IF wherein $R^1$ and $R^2$ are each non-hydrogen substituents independently selected from the same group as defined in Formula I above;

$R^3$, Y and n are the same as defined in Formula I above;

X is optionally alicyclic, optionally substituted carbocyclic aryl; optionally substituted heteroalicyclic, optionally substituted heteroaromatic, optionally substituted heteroaralkyl, or optionally substituted heteroalicyclicalkyl group, each preferably having 3–10 carbon or hetero atoms in a ring, more preferably 5 or 6 membered ring(s), and 1–3 N, O or S atoms; $R^5$ and $R^6$ are independently hydrogen, optionally substituted alkyl preferably having 1 to about 20 carbons, more preferably 1 to about 12 carbons; optionally substituted alkenyl preferably having 2 to about 20 carbon atoms, more preferably 2 to about 12 carbon atoms; optionally substituted alkynyl preferably having 2 to about 20 carbon atoms, more preferably 2 to about 12 carbon atoms; optionally substituted carbocyclic aryl having at least about 6 ring carbon atoms; optionally substituted aralkyl having at least about 6 ring carbon atoms; optionally substituted heteroaromatic or heteroalicyclic group 1 to 3 rings, 3 to 8 ring members in each ring and from 1 to 3 hetero atoms (particularly 1–3 N, O and/or S atoms); or optionally substituted heteroaralkyl or heteroalicyclicalkyl group having from 1 to 3 rings, 3 to 8 ring members in each ring and from 1 to 3 hetero atoms (particularly 1–3 N, O and/or S atoms), more preferably one of $R^5$ and $R^6$ is hydrogen; and Q is omitted (it does not exist) or is —(CH2)p-CO-A-$R^7$ wherein p is 0, 1 or 2 A is O or NH and $R^7$ is independently hydrogen, optionally substituted alkyl preferably having 1 to about 20 carbons, more preferably 1 to about 12 carbons; optionally substituted alkenyl preferably having 2 to about 20 carbon atoms, more preferably 2 to about 12 carbon atoms; optionally substituted alkynyl preferably having 2 to about 20 carbon atoms, more preferably 2 to about 12 carbon atoms; optionally substituted carbocyclic aryl having at least about 6 ring carbon atoms; optionally substituted aralkyl having at least about 6 ring carbon atoms; optionally substituted heteroaromatic or heteroalicyclic group 1 to 3 rings, 3 to 8 ring members in each ring and from 1 to 3 hetero atoms; (particularly 1–3 N, O and/or S atoms); or optionally substituted heteroaralkyl or heteroalicyclicalkyl group having from 1 to 3 rings, 3 to 8 ring members in each ring and from 1 to 3 hetero atoms (particularly 1–3 N, O and/or S atoms); and pharmaceutically acceptable salts thereof Preferred $R^1$ groups of pyrazole compounds of Formulae I, I', IA, IB, IC, ID, IE and IF are optionally substituted alkyl, optionally substituted carbocyclic aryl, optionally substituted aralkyl (or aryalkyl) such as optionally substituted benzyl, and optionally substituted heteroaromatic, particularly optionally substituted phenyl, benzyl, pyridyl and naphthyl. Generally preferred $R^1$ groups include $C_{1-16}$ alkyl, branched alkyl such as propyl, butyl, pentyl, and the like, particularly branched alkyl such as i-propyl, t-butyl, sec-pentyl and the like, and optionally substituted phenyl such as phenyl having one or more $C_{1-16}$ alkyl substituents e.g. propyl, butyl including t-butyl, and the like. Particularly preferred $R^1$ groups have more significant size (molecular volume) such as $C_{4-16}$ alkyl preferably branched such as t-butyl, isopentyl and the like, and substituted carbocyclic aryl, particularly with branched ring substituents such phenyl substituted with t-butyl, isopentyl, trifluoromethyl, $CF_3CH_2$—, and the like.

Preferred $R^2$ groups of compounds of Formulae I, I', IA, IB, IC, ID, IE and IF include optionally substituted carbocyclic aryl, particularly optionally substituted phenyl and naphthyl, and optionally substituted heteroaromatic and heteroalicyclic, particularly nitrogen-containing heterocyclics such as pyridyl, tetrahydropyridyl, quinoline, isoquinoline, piperidine and the like.

Preferred X linker groups of compounds of Formulae I, I', IA, IB and ID are alkylene groups, particularly alkylene groups having 2, 3, 4, 5, or 6 chain carbon atoms (i.e. —CH$_2$—), more preferably 4 or 5 chain carbon atoms. Preferred X linkers groups of compounds of Formula I, I' IA, IB and ID include carbocyclic aryl, heteroaromatic, alicyclic and heteroalicyclic groups, particularly groups having 3 to 10 ring members, more particularly 4–6 membered rings, such as optionally substituted phenyl, thienyl, furyl, pyrrolyl and pyridyl groups. Carbonyl is a preferred Y group.

Preferred Z groups of compounds of Formulae I, I', IA, IB, IC, ID, IE and IF comprise hydroxy moieties, particularly phenolic moieties. Substituted amines and natural and non-natural amino acids are generally preferred Z groups. For example, preferred Z groups include optionally substituted C$_{1-12}$ alkylamine, preferably substituted with a phenolic group on the alkyl chain, such as —NH(CH$_2$)$_{1-8}$C$_6$H$_4$OH. Preferred Z groups include tyrosine groups and other aminophenyl groups such as —NHCH(CH$_2$C$_6$H$_4$OH)C(=O)NH$_2$; —NH{CH$_2$C$_6$H$_3$—(N=C—NH—)}C(=O)NH$_2$; NH{CH$_2$C$_6$H$_3$—(N=N—NH—)}C(=O)NH$_2$ where in such groups the phenolic moiety may be substituted at any available phenyl ring position, and preferably the hydroxyl is a meta or para substituent. Specifically preferred Z groups including tyrosine, homo-tyrosine, 4-hydroxy-α-phenylglycine, 4-amino-phenylalanine, 4-hydroxymethyl-phenylalanine, 4-acetyl-amino-phenylalanine, meta-tyrosine, β-homo-tyrosine, threonine, serine, and 4-hydroxy-phenyl-ethylamine.

Also, unless otherwise indicated herein, it is understood that the above Formulae I, I' IA, IB, IC, ID, IE and IF are inclusive of all possible regio isomers of the depicted pyrazoles, even in the case of Formulae IA, IB, IC, ID, IE and IF where the preferred regio isomer is depicted.

Particular compounds of the invention include:

N-{5-[1-(4-tert-butylphenyl)-3-pyridin-2-yl-1H-pyrazol-5-yl]pentanoyl}tyrosinamide;
N-{5-[1-(4-tert-butylphenyl)-3-pyridin-3-yl-1H-pyrazol-5-yl]pentanoyl}tyrosinamide;
N-{5-[1-(4-tert-butylphenyl)-5-pyridin-3-yl-1H-pyrazol-3-yl]pentanoyl}tyrosinamide;
N-{5-[1-(4-tert-butylphenyl)-3-pyridin-4-yl-1H-pyrazol-5-yl]pentanoyl}tyrosinamide;
N-{5-[1-(4-tert-butylphenyl)-5-pyridin-4-yl-1H-pyrazol-3-yl]pentanoyl}tyrosinamide;
N-{5-[1-(4-tert-butylphenyl)-3-pyridin-3-yl-1H-pyrazol-5-yl]pentanoyl}-N,N-dimethyltyrosinamide.
N-(3-[1-(4-tert-butylphenyl)-5-pyridin-3-yl-1H-pyrazol-3-yl]propanoyl)tyrosinamide;
N-(3-[1-(4-tert-butylphenyl)-3-pyridin-3-yl-1H-pyrazol-5-yl]propanoyl)tyrosinamide
N-[4-(1-butyl-3-isoquinolin-3-yl-1H-pyrazol-5-yl)benzoyl]tyrosinamide;
N-{5-[1-(4-isopropylphenyl)-3-pyridin-3-yl-1H-pyrazol-5-yl]pentanoyl}tyrosinamide;
N-{6-[1-(4-isopropylphenyl)-3-pyridin-2-yl-1H-pyrazol-5-yl]hexanoyl}tyrosinamide
N-{6-[1-(4-tert-butylphenyl)-3-pyridin-2-yl-1H-pyrazol-5-yl]hexanoyl}-3-hydroxyphenylalaninamide;
N-[1-(aminocarbonyl)-3-(4-hydroxyphenyl)propyl]-5-[1-(4-tert-butylphenyl)-3-pyridin-2-yl-1H-pyrazol-5-yl]pentanamide;
N-[5-(1-butyl-3-isoquinolin-3-yl-1H-pyrazol-5-yl)pentanoyl]tyrosinamide;
N-{6-[1-(4-tert-butylphenyl)-3-pyridin-2-yl-1H-pyrazol-5-yl]hexanoyl}serinamide;
N-{6-[1-(4-iso-propylphenyl)-3-pyridin-2-yl-1H-pyrazol-5-yl]hexanoyl}serinamide;
N-{6-[1-(4-iso-propylphenyl)-3-pyridin-2-yl-1H-pyrazol-5-yl]hexanoyl}threonamide;
N-{5-[1-(4-isopropylphenyl)-3-pyridin-2-yl-1H-pyrazol-5-yl]pentanoyl}tyrosinamide;
6-[1-(4-tert-butylphenyl)-3-pyridin-2-yl-1H-pyrazol-5-yl]-N-[2-(4-hydroxyphenyl)ethyl]hexanamide;
N-{6-[1-(4-tert-butylphenyl)-3-pyridin-2-yl-1H-pyrazol-5-yl]hexanoyl}tyrosinamide;
N-{5-[1-(4-tert-butylphenyl)-3-isoquinolin-3-yl-1H-pyrazol-5-yl]pentanoyl}tyrosinamide;
N-{6-[1-(4-tert-butylphenyl)-3-isoquinolin-3-yl-1H-pyrazol-5-yl]hexanoyl}tyrosinamide;
N-{6-[1-(4-tert-butylphenyl)-3-pyridin-2-yl-1H-pyrazol-5-yl]hexanoyl}-N-methyltyrosinamide;
N-{6-[1-(4-tert-butylphenyl)-3-pyridin-2-yl-1H-pyrazol-5-yl]hexanoyl}-4-(hydroxymethyl)phenylalaninamide;
4-amino-N-{6-[1-(4-tert-butylphenyl)-3-pyridin-2-yl-1H-pyrazol-5-yl]hexanoyl}phenylalaninamide;
4-(acetylamino)-N-{6-[1-(4-tert-butylphenyl)-3-pyridin-2-yl-1H-pyrazol-5-yl]hexanoyl}phenylalaninamide;
4-(aminocarbonyl)-N-{6-[1-(4-tert-butylphenyl)-3-pyridin-2-yl-1H-pyrazol-5-yl]hexanoyl}phenylalaninamide;
N-butyl-N-{6-[1-(4-tert-butylphenyl)-3-pyridin-2-yl-1H-pyrazol-5-yl]hexanoyl}tyrosinamide;
N-{6-[1-(4-tert-butylphenyl)-3-pyridin-2-yl-1H-pyrazol-5-yl]hexanoyl}threonamide;
N-[2-amino-1-(4-hydroxyphenyl)-2-oxoethyl]-6-[1-(4-tert-butylphenyl)-3-pyridin-2-yl-1H-pyrazol-5-yl]hexanamide;
N-{2-[4-(aminosulfonyl)phenyl]ethyl}-5-[1-(4-tert-butylphenyl)-3-pyridin-2-yl-1H-pyrazol-5-yl]pentanamide;
N-({5-[1-(4-isopropylphenyl)-3-pyridin-2-yl-1H-pyrazol-5-yl]thien-2-yl}carbonyl)tyrosinamide;
N-[2-amino-1-(4-hydroxyphenyl)-2-oxoethyl]-4-[1-(4-tert-butylphenyl)-3-pyridin-2-yl-1H-pyrazol-5-yl]benzamide;
4-[1-(4-tert-butylphenyl)-3-pyridin-2-yl-1H-pyrazol-5-yl]-N-[2-(4-hydroxyphenyl)ethyl]benzamide;
N-{3-[1-(4-tert-butylbenzyl)-3-isoquinolin-3-yl-1H-pyrazol-5-yl]benzoyl}tyrosinamide;
N-{5-[1-(4-tert-butylphenyl)-3-pyridin-4-yl-1H-pyrazol-5-yl]pentanoyl}tyrosinamide;
N-{3-[1-(4-tert-butylbenzyl)-3-pyridin-3-yl-1H-pyrazol-5-yl]benzoyl}tyrosinamide;
N-{3-[1-(4-tert-butylphenyl)-3-isoquinolin-3-yl-1H-pyrazol-5-yl]benzoyl}tyrosinamide;
N-[4-(1-butyl-3-isoquinolin-3-yl-1H-pyrazol-5-yl)benzoyl]tyrosinamide;
N-{3-[1-(4-tert-butylbenzyl)-3-quinolin-3-yl-1H-pyrazol-5-yl]benzoyl}tyrosinamide;
N-{3-[3-isoquinolin-3-yl-1-(4-propylphenyl)-1H-pyrazol-5-yl]benzoyl}tyrosinamide;
N-{5-[1-(4-tert-butylphenyl)-3-pyridin-3-yl-1H-pyrazol-5-l]pentanoyl}tyrosinamide;
N-{3-[1-(4-tert-butylphenyl)-3-pyridin-3-yl-1H-pyrazol-5-yl]benzoyl}tyrosinamide;
N-{4-[1-(4-tert-butylphenyl)-3-pyridin-3-yl-1H-pyrazol-5-yl]benzoyl}tyrosinamide;
N-{5-[1-(4-tert-butylbenzyl)-3-pyridin-4-yl-1H-pyrazol-5-yl]pentanoyl}tyrosinamide;
N-{3-[1-(4-tert-butylbenzyl)-3-pyridin-4-yl-1H-pyrazol-5-yl]benzoyl}tyrosinamide;
N-{5-[1-(4-tert-butylbenzyl)-3-pyridin-3-yl-1H-pyrazol-5-yl]pentanoyl}tyrosinamide;

N-{5-[1-(4-tert-butylphenyl)-3-pyridin-4-yl-1H-pyrazol-5-yl]pentanoyl}tyrosinamide;
N-[3-(1-butyl-3-isoquinolin-3-yl-1H-pyrazol-5-yl)benzoyl]tyrosinamide;
N-(4-{[1-(4-tert-butylphenyl)-3-pyridin-4-yl-1H-pyrazol-5-yl]amino}butanoyl)tyrosinamide;
N-[(1-butyl-3-pyridin-3-yl-1H-pyrazol-5-yl)methyl]glycyltyrosinamide;
N-{[1-(4-tert-butylphenyl)-3-pyridin-3-yl-1H-pyrazol-5-yl]methyl}glycyltyrosinamide;
N-[(1-butyl-3-pyridin-3-yl-1H-pyrazol-5-yl)methyl]-beta-alanyltyrosinamide;
N-(3-{[(1-butyl-3-pyridin-3-yl-1H-pyrazol-5-yl)methyl]amino}benzoyl)tyrosinamide;
N-[3-({[1-(4-tert-butylphenyl)-3-pyridin-4-yl-1H-pyrazol-5-yl]methyl}amino)benzoyl]tyrosinamide;
N-({1-[(1-butyl-3-pyridin-3-yl-1H-pyrazol-5-yl)methyl]piperidin-4-yl}carbonyl)tyrosinamide;
N-[(1-{[1-(4-tert-butylphenyl)-3-pyridin-3-yl-1H-pyrazol-5-yl]methyl}piperidin-4-yl)carbonyl]tyrosinamide;
N-2--{[1-(4-tert-butylphenyl)-3-pyridin-3-yl-1H-pyrazol-5-yl]methyl}-N~1~-[2-(4-hydroxyphenyl)ethyl]glycinamide;
N-3-[(1-butyl-3-pyridin-3-yl-1H-pyrazol-5-yl)methyl]-N~1~-[2-(4hydroxyphenyl)ethyl]-beta-alaninamide;
4-{[(1-butyl-3-pyridin-3-yl-1H-pyrazol-5-yl)methyl]amino}-N-[2-(4-hydroxyphenyl)ethyl]benzamide; or an optically active isomer, racemate or tautomer thereof, and/or a pharmaceutically acceptable salts thereof.

Additional preferred compound include:
N-({3-[1-(4-tert-butylphenyl)-3-pyridin-4-yl-1H-pyrazol-5-yl]propoxy}acetyl)}tyrosinamide;
4[-2-({3-[1-(4-tert-butylphenyl)-3-pyridin-4-yl-1H-pyrazol-5-yl]propyl}amino)ethyl]phenol;
N-{3-[1-(4-tert-butylphenyl)-3-pyridin-4-yl-1H-pyrazol-5-yl]propyl}tyrosinamide;
N-acetyl-N-{3-[1-(4-tert-butylphenyl)-3-pyridin-4-yl-1H-pyrazol-5-yl]propyl}tyrosinamide;
N-({3-[1-(4-tert-butylphenyl)-3-pyridin-4-yl-1H-pyrazol-5-yl]propoxy}acetyl)tyrosinamide;
4-[2-({3-[1-(4-tert-butylphenyl)-3-pyridin-4-yl-1H-pyrazol-5-yl]propyl}amino)ethyl]phenol;
N-{3-[1-(4-tert-butylphenyl)-3-pyridin-4-yl-1H-pyrazol-5-yl]propyl}tyrosinamide;
N-acetyl-N-{3-[1-(4-tert-butylphenyl)-3-pyridin-4-yl-1H-pyrazol-5-yl]propyl}tyrosinamide;
3-[(4-{[1-(4-tert-butylphenyl)-3-pyridin-4-yl-1H-pyrazol-5-yl]amino}butanoyl)amino]-4-(4-hydroxyphenyl)butanamide;
N-(4-{[1-(4-tert-butylphenyl)-3-(1-methyl-1,2,3,6-tetrahydropyridin-4-yl)-1H-pyrazol-5-yl]amino}butanoyl)tyrosinamide;
N-(3-{[1-(4-tert-butylphenyl)-3-pyridin-4-yl-1H-pyrazol-5-yl]amino}propyl)tyrosinamide;
N-acetyl-N-(3-{[1-(4-tert-butylphenyl)-3-pyridin-4-yl-1H-pyrazol-5-yl]amino}propyl)tyrosinamide;
N-(4-{[1-(4-tert-butylphenyl)-3-(1-oxidopyridin-4-yl)-1H-pyrazol-5-yl]amino}butanoyl)tyrosinamide;
4-{[1-(4-tert-butylphenyl)-3-pyridin-4-yl-1H-pyrazol-5-yl]amino}-N-[2-(4-hydroxyphenyl)ethyl]butanamide;
4-{2-[(4-{[1-(4-tert-butylphenyl)-3-pyridin-4-yl-1H-pyrazol-5-yl]amino}butyl)amino]ethyl}phenol;
N-(4-{[1-(4-tert-butylphenyl)-3-pyridin-4-yl-1H-pyrazol-5-yl]amino}butanoyl)-N-(2-hydroxyethyl)tyrosinamide;
N-(4-{[1-(4-tert-butylphenyl)-3-pyridin-4-yl-1H-pyrazol-5-yl]amino}butanoyl)-N-[2-(1-methylpyrrolidin-2-yl)ethyl]tyrosinamide;
N-(4-{[1-(4-tert-butylphenyl)-3-pyridin-3-yl-1H-pyrazol-5-yl]amino}butanoyl)tyrosinamide;
N-(4-{[1-(4-tert-butylphenyl)-3-(1-methyl-1,2,5,6-tetrahydropyridin-3-yl)-1H-pyrazol-5-yl]amino}butanoyl)tyrosinamide;
(3R)-3-[(4-{[1-(4-tert-butylphenyl)-3-pyridin-3-yl-1H-pyrazol-5-yl]amino}butanoyl)amino]-4-(4-hydroxyphenyl)butanamide;
N-(3-{[1-(4-tert-butylphenyl)-3-pyridin-3-yl-1H-pyrazol-5-yl]amino}propyl)tyrosinamide;
N-acetyl-N-(3-{[1-(4-tert-butylphenyl)-3-pyridin-3-yl-1H-pyrazol-5-yl]amino}propyl)tyrosinamide;
N-(4-{[1-(4-tert-butylphenyl)-3-(1-oxidopyridin-3-yl)-1H-pyrazol-5-yl]amino}butanoyl)tyrosinamide;
4-{[1-(4-tert-butylphenyl)-3-pyridin-3-yl-1H-pyrazol-5-yl]amino}-N-[2-(4-hydroxyphenyl)ethyl]butanamide;
4-{2-[(4-{[1-(4-tert-butylphenyl)-3-pyridin-3-yl-1H-pyrazol-5-yl]amino}butyl)amino]ethyl}phenol;
N-(4-{[1-(4-tert-butylphenyl)-3-pyridin-3-yl-1H-pyrazol-5-yl]amino}butanoyl)-N-(2-hydroxyethyl)tyrosinamide;
N-(4-{[1-(4-tert-butylphenyl)-3-pyridin-3-yl-1H-pyrazol-5-yl]amino}butanoyl)-N-[2-(1-methylpyrrolidin-2-yl)ethyl]tyrosinamide;
N-(4-{[1-(4-tert-butylphenyl)-3-pyridin-3-yl-1H-pyrazol-5-yl]oxy}butanoyl)tyrosinamide; or an optically active isomer, racemate or tautomer thereof, and/or a pharmaceutically acceptable salts thereof.

Substituted pyrazole compounds of the invention are useful for treatment of infertility in male and female mammals, particularly humans. Therapeutic methods of the invention in general comprise administering an effective amount of one or more substituted pyrazole compounds as disclosed herein to a mammal in need thereof, such as a mammal suspected of suffering from infertility, particularly a human suspected of suffering from infertility. Compounds of the invention will be useful for treatment of infertility conditions currently treated with FSH and/or LH, including female infertility and male spermatogenesis disorders.

Additionally, in contrast to current protein therapeutics such as FSH, compounds of the invention can be administered orally and without extensive medical specialist supervision.

Preferred compounds of the invention exhibit good agonist activity in standard Follicle Stimulating Hormone (FSH) assays, such as the assay of Example 9 which follows.

It also has been found that substituted pyrazole compounds of the invention exhibit good inhibition activity against phosphodiesterase PDE4, adenosine transporters, and prostanoid receptors. Accordingly, methods are provided for treatment of diseases and disorders associated with phosphodiesterase PDE4, adenosine transporters, and prostanoid receptors, which methods in general comprise administration of an effective amount of one or more substituted pyrazole compounds to a patient (e.g. mammal, such as human or other primate) in need of such treatment.

The invention also provides pharmaceutical compositions that comprise one or more substituted pyrazole compounds of the invention and a suitable carrier for the compositions. Other aspects of the invention are disclosed infra.

DETAILED DESCRIPTION OF THE INVENTION

We have now discovered that substituted pyrazole compounds, including compounds of the above Formulae I, I', IA, IB, IC, ID, IE and IF, that are useful for treatment of infertility in mammals, including female and male humans.

Suitable alkyl substituent groups of compounds of the invention (which includes compounds of Formulae I, I', IA, IB, IC, ID, IE and IF as defined above) typically have from 1 to about 12 carbon atoms, more preferably 1 to about 8 carbon atoms, still more preferably 1, 2, 3, 4, 5, or 6 carbon atoms. As used herein, the term alkyl unless otherwise modified refers to both cyclic and noncyclic groups, although of course cyclic groups will comprise at least three carbon ring members. Preferred alkenyl and alkynyl groups of compounds of the invention have one or more unsaturated linkages and typically from 2 to about 12 carbon atoms, more preferably 2 to about 8 carbon atoms, still more preferably 2, 3, 4, 5, or 6 carbon atoms. The terms alkenyl and alkynyl as used herein refer to both cyclic and noncyclic groups, although straight or branched noncyclic groups are generally more preferred. Preferred alkoxy groups of compounds of the invention include groups having one or more oxygen linkages and from 1 to about 12 carbon atoms, more preferably from 1 to about 8 carbon atoms, and still more preferably 1, 2, 3, 4, 5 or 6 carbon atoms. Preferred alkylthio groups of compounds of the invention include those groups having one or more thioether linkages and from 1 to about 12 carbon atoms, more preferably from 1 to about 8 carbon atoms, and still more preferably 1, 2, 3, 4, 5, or 6 carbon atoms. Preferred alkylsulfinyl groups of compounds of the invention include those groups having one or more sulfoxide (SO) groups and from 1 to about 12 carbon atoms, more preferably from 1 to about 8 carbon atoms, and still more preferably 1, 2, 3, 4, 5, or 6 carbon atoms. Preferred alkylsulfonyl groups of compounds of the invention include those groups having one or more sulfonyl ($SO_2$) groups and from 1 to about 12 carbon atoms, more preferably from 1 to about 8 carbon atoms, and still more preferably 1, 2, 3, 4, 5 or 6 carbon atoms. Preferred aminoalkyl groups include those groups having one or more primary, secondary and/or tertiary amine groups, and from 1 to about 12 carbon atoms, more preferably 1 to about 8 carbon atoms, still more preferably 1, 2, 3, 4, 5, or 6 carbon atoms. Secondary and tertiary amine groups are generally more preferred than primary amine moieties. Suitable heteroaromatic groups of compounds of the invention contain one or more N, O or S atoms and include, e.g., coumarinyl including 8-coumarinyl, quinolinyl including 8-quinolinyl, pyridyl, pyrazinyl, pyrimidyl, furyl, pyrrolyl, thienyl, thiazolyl, oxazolyl, oxidizolyl, triazole, imidazolyl, indolyl, benzofuranyl and benzothiazole. Suitable heteroalicyclic groups of compounds of the invention contain one or more N, O or S atoms and include, e.g., tetrahydrofuranyl, thienyl, tetrahydropyranyl, piperidinyl, morpholino and pyrrolidinyl groups. Suitable carbocyclic aryl groups of compounds of the invention include single and multiple ring compounds, including multiple ring compounds that contain separate and/or fused aryl groups. Typical carbocyclic aryl groups of compounds of the invention contain 1 to 3 separate or fused rings and from 6 to about 18 carbon ring atoms. Specifically preferred carbocyclic aryl groups include phenyl; naphthyl including 1-naphthyl and 2-naphthyl; biphenyl; phenanthryl; anthracyl; and acenaphthyl. Substituted carbocyclic groups are particularly suitable including substituted phenyl, such as 2-substituted phenyl, 3-substituted phenyl, 4-substituted phenyl, 2,3-substituted phenyl, 2,4-substituted phenyl, and 2,4-substituted phenyl; and substituted naphthyl, including naphthyl substituted at the 5, 6 and/or 7 positions.

Suitable aralkyl groups of compounds of the invention include single and multiple ring compounds, including multiple ring compounds that contain separate and/or fused aryl groups. Typical aralkyl groups contain 1 to 3 separate or fused rings and from 6 to about 18 carbon ring atoms. Preferred aralkyl groups include benzyl and methylenenaphthyl (—$CH_2$-naphthyl), and other carbocyclic aralkyl groups, as discussed above.

Suitable heteroaralkyl groups of compounds of the invention include single and multiple ring compounds, including multiple ring compounds that contain separate and/or fused heteroaromatic groups, where such groups are substituted onto an alkyl linkage. More preferably, a heteroaralkyl group contains a heteroaromatic group that has 1 to 3 rings, 3 to 8 ring members in each ring and from 1 to 3 hetero (N, O or S) atoms, substituted onto an alkyl linkage. Suitable heteroaromatic groups substituted onto an alkyl linkage include e.g., coumarinyl including 8-coumarinyl, quinolinyl including 8-quinolinyl, pyridyl, pyrazinyl, pyrimidyl, furyl, pyrrolyl, thienyl, thiazolyl, oxazolyl, oxidizolyl, triazole, imidazolyl, indolyl, benzofuranyl and benzothiazole.

Suitable heteroalicyclicalkyl groups of compounds of the invention include single and multiple ring compounds, where such groups are substituted onto an alkyl linkage. More preferably, a heteroalicylicalkyl group contains at least one ring that has 3 to 8 ring members from 1 to 3 hetero (N, O or S) atoms, substituted onto an alkyl linkage. Suitable heteroalicyclic groups substituted onto an alkyl linkage include e.g. tetrahydrofuranyl, thienyl, tetrahydropyranyl, piperidinyl, morpholino and pyrrolidinyl groups.

As discussed above, particularly preferred X linker groups are alkylene, particularly having 4 or 5 chain carbons, such as —$CH_2CH_2CH_2CH_2$— and —$CH_2CH_2CH_2CH_2CH_2$—. X linker groups may one contain one or more carbon-carbon double or triple bonds in the chain, i.e. a alkenylene, alkynylene, heteroalkenylene or heteroalkynylene linkage. Such unsaturated X groups typically contain 1, 2 or 3 carbon-carbon multiple bonds, more typically 1 or 2 carbon-carbon multiple bonds. An X group that is heteroalkylene, heteroalkenylene, or heteroalkynylene contains one or more N, O or S atoms in the linker chain, more typically 1 or 2 N, O or S atoms in the chain. An X linker group also preferably may be carbocyclic aryl or a heteroaromatic group, particularly 3–10 membered rings or fused rings, more particularly 4, 5 and 6 membered rings with zero, one or more N, O, or S atoms such as optionally substituted o-, m-, p-phenyl, pyridyl, furyl, thiophenyl and pyrrolidinyl rings.

As discussed above, R, $R^1$, $R^2$, $R^3$, $R^4$, $R^5$, $R^6$, $R^7$, X, Y and Z groups are optionally substituted. A "substituted" R, $R^1$, $R^2$, $R^3$, $R^4$, $R^5$, $R^6$, $R^7$, X, Y and Z group or other substituent may be substituted by other than hydrogen at one or more available positions, typically 1 to 3 or 4 positions, by one or more suitable groups such as those disclosed herein. Suitable groups that may be present on a "substituted" R, $R^1$, $R^2$, $R^3$, $R^4$, $R^5$, $R^6$, $R^7$, X, Y and Z group or other substituent include e.g. halogen such as fluoro, chloro, bromo and iodo; cyano; hydroxyl; nitro; azido; alkanoyl such as a $C_{1-6}$ alkanoyl group such as acyl and the like; carboxamido; alkyl groups including those groups having 1 to about 12 carbon atoms, or 1, 2, 3, 4, 5, or 6 carbon atoms; alkenyl and alkynyl groups including groups having one or more unsaturated linkages and from 2 to about 12 carbon, or 2, 3, 4, 5 or 6 carbon atoms; alkoxy groups having those having one or more oxygen linkages and from 1 to about 12 carbon atoms, or 1, 2, 3, 4, 5 or 6 carbon atoms; aryloxy such as phenoxy; alkylthio groups including those moieties having one or more thioether linkages and from 1 to about 12 carbon atoms, or 1, 2, 3, 4, 5 or 6 carbon atoms; alkylsulfinyl groups including those moieties having one or more sulfinyl linkages and from 1 to about 12 carbon atoms, or 1, 2, 3, 4, 5, or 6 carbon atoms; alkylsulfonyl groups including those moieties having one or more sulfonyl linkages and from 1 to about 12 carbon atoms, or 1, 2, 3, 4, 5, or 6 carbon atoms; aminoalkyl groups such as groups having one or more N atoms and from 1 to about 12 carbon atoms, or 1, 2, 3, 4, 5 or 6 carbon atoms; carbocyclic aryl having 6 or more carbons, particularly phenyl (e.g. an R group being a substituted or unsubstituted biphenyl moiety); aralkyl having 1 to 3 separate or fused rings and from 6 to about 18 carbon ring atoms, with benzyl being a preferred group; aralkoxy having 1 to 3 separate or fused rings and from 6 to about 18 carbon ring atoms, with O-benzyl being a preferred group; or a heteroaromatic or heteroalicyclic group having 1 to 3 separate or fused rings with 3 to about 8 members per ring and one or more N, O or S atoms, e.g. coumarinyl, quinolinyl, pyridyl, pyrazinyl, pyrimidyl, furyl, pyrrolyl, thienyl, thiazolyl, oxazolyl, imidazolyl, indolyl, benzofuranyl, benzothiazolyl, tetrahydrofuranyl, tetrahydropyranyl, piperidinyl, morpholino and pyrrolidinyl.

Preferred carbocyclic or heteroaromatic ring substituents of compounds of the invention include halogen (F, Cl, Br and I; hydroxyl; azido; optionally substituted alkyl having 1 to about 12 carbons such as methyl, ethyl, propyl and butyl and branched groups such as isopropyl, sec-butyl and tert-butyl, and including halogenated alkyl, particularly fluoro-alkyl having 1 to about 6 carbon atoms; optionally substituted alkoxy having 1 to about 12 carbons such as methoxy, ethoxy, propoxy and butoxy, and including halogenated alkoxy, particularly fluoro-alkoxy having 1 to about 6 carbon atoms; optionally substituted alkylthio having 1 to about 6 carbons such as methylthio and ethylthio; optionally substituted alkylsulfinyl having 1 to about 6 carbons such as methylsulfinyl (—S(O)CH$_3$) and ethylsulfinyl (—S(O)CH$_2$CH$_3$); optionally substituted alkylsulfonyl having 1 to about 6 carbons such as methylsulfonyl (—S(O)$_2$CH$_3$) and ethylsulfonyl (—S(O)$_2$CH$_2$CH$_3$); and optionally substituted arylalkoxy such as benzyloxy (C$_6$H$_5$CH$_2$O—).

It should be understood that alkoxy, alkylthio, alkylsulfinyl, alkylsulfonyl and aminoalkyl substituent groups described above include groups where a hetero atom is directly bonded to a ring system, such as a carbocyclic aryl group or a heteroalicyclic or heteroaromatic group, as well as groups where a hetero atom of the group is spaced from such ring system by an alkylene linkage, e.g. of 1 to about 4 carbon atoms.

Specifically preferred compounds of the invention include the following depicted compounds, and pharmaceutically acceptable salts of these compounds. Results (EC$_{50}$ values, expressed as μM) for certain compounds in the FSH assay of Example 9 are set forth immediately right of the depicted compound structure.

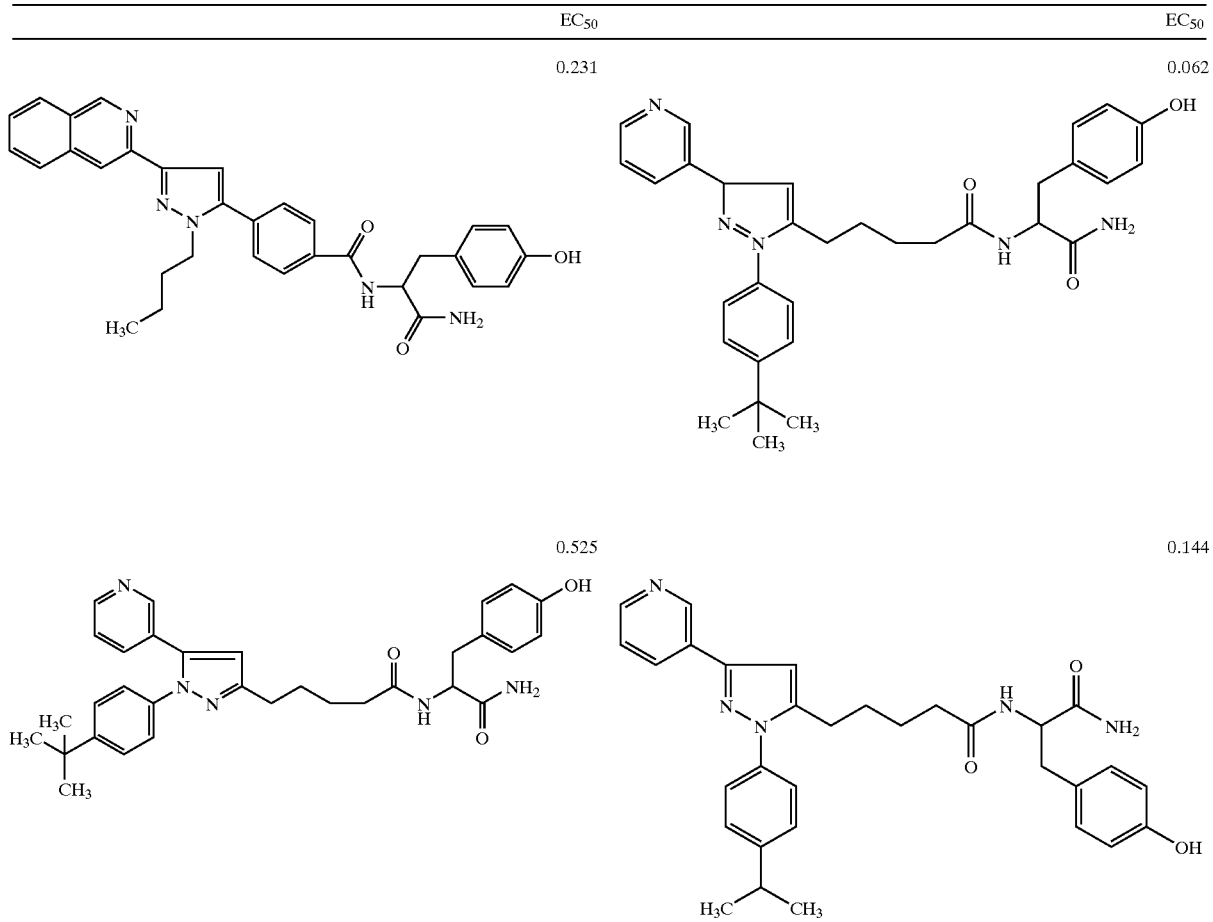

-continued
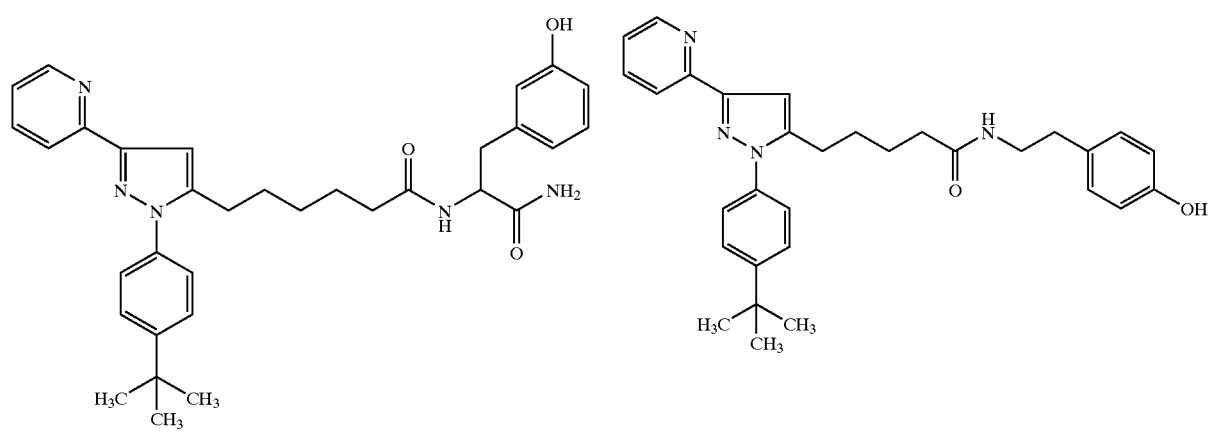
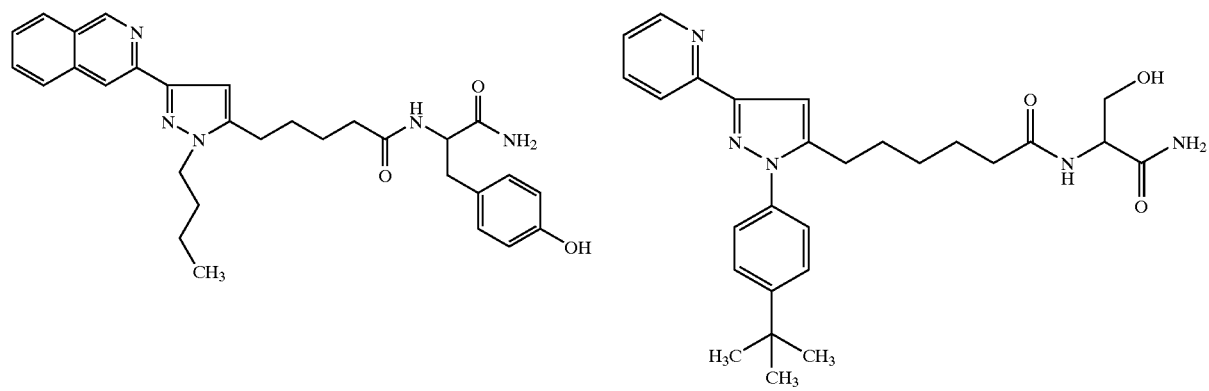
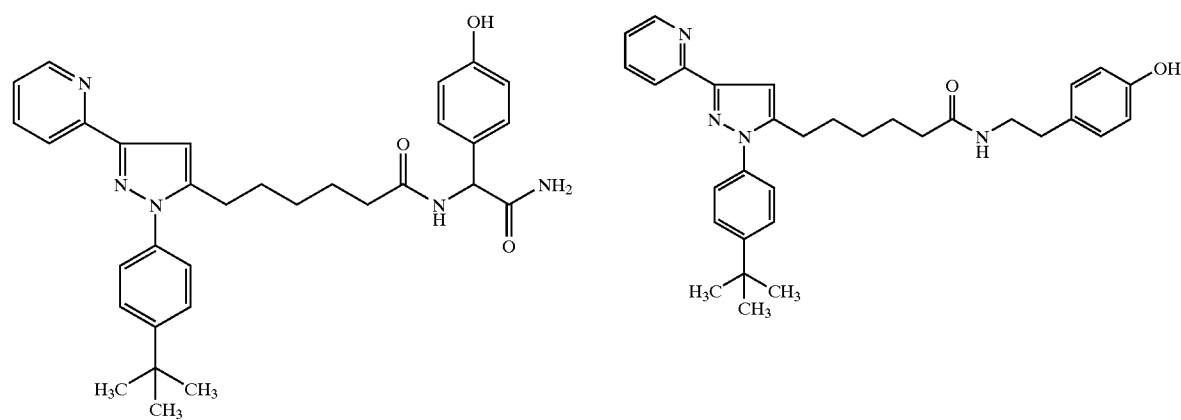
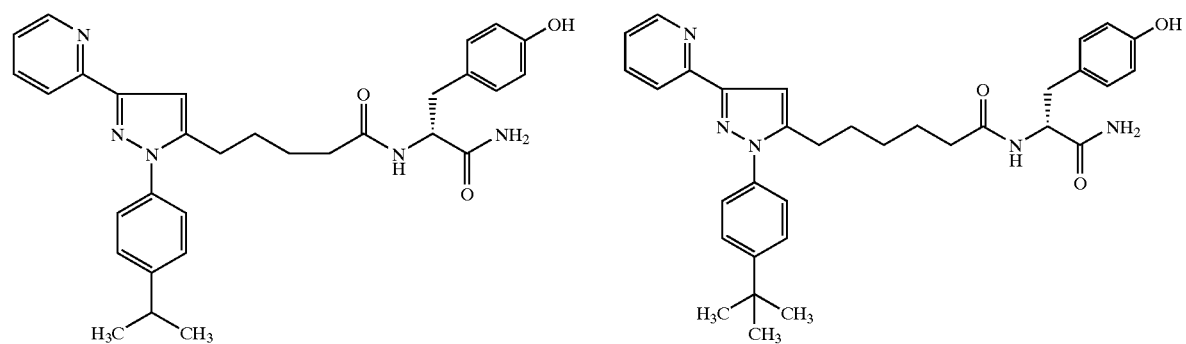

-continued
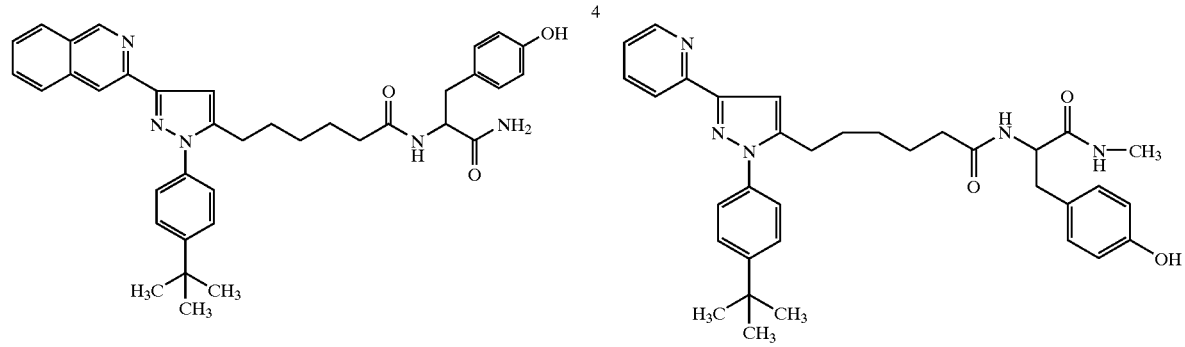
4
4.3
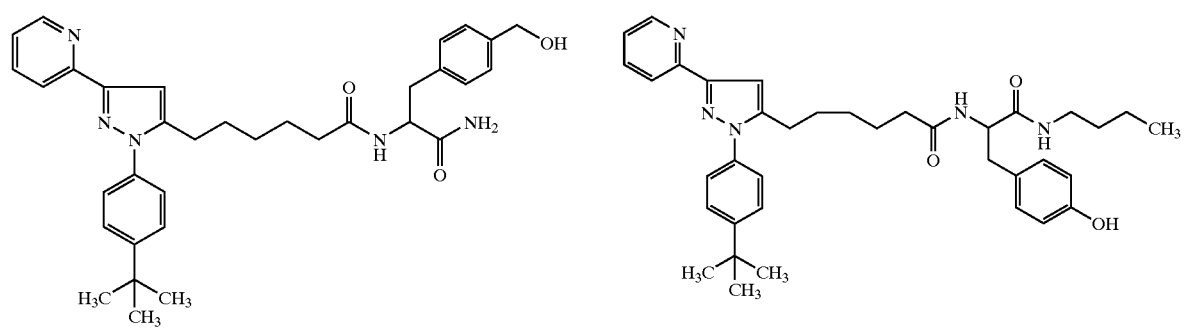
6.25
4.5
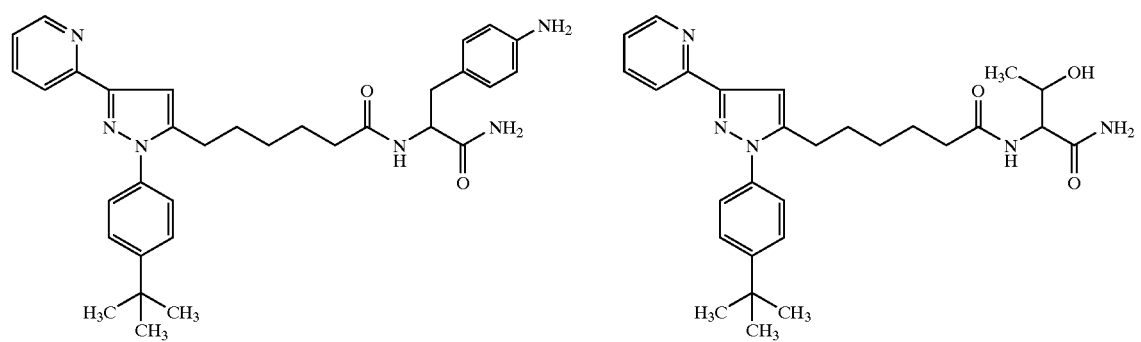
6.25
6.25
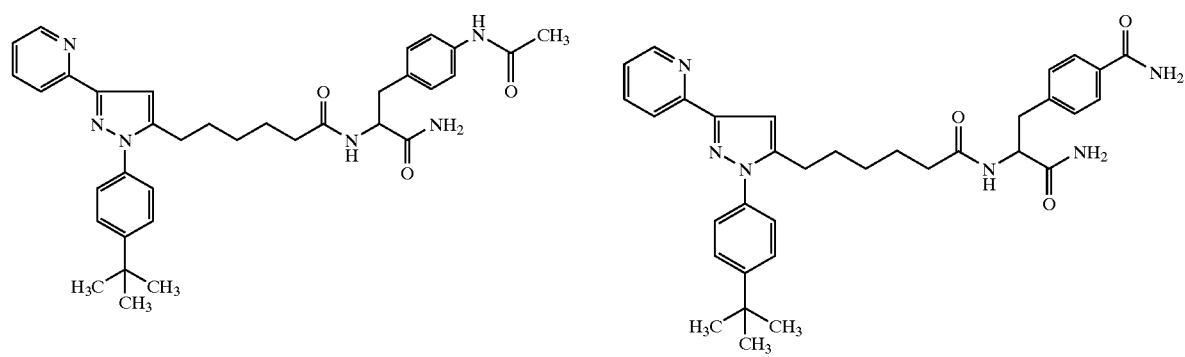
12.5

-continued
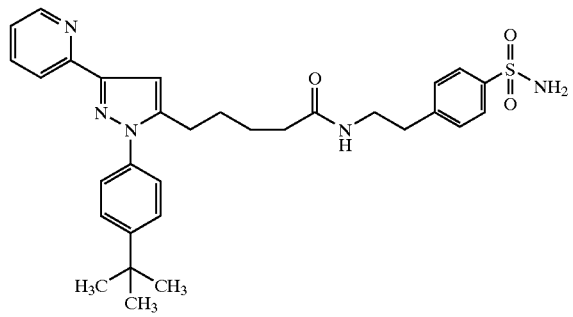
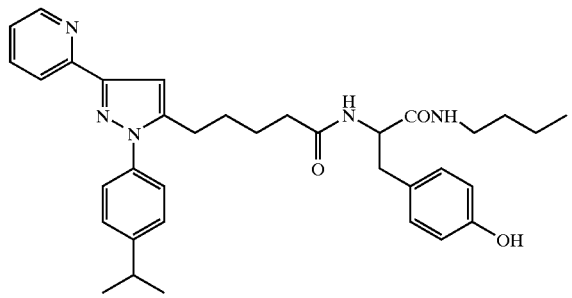
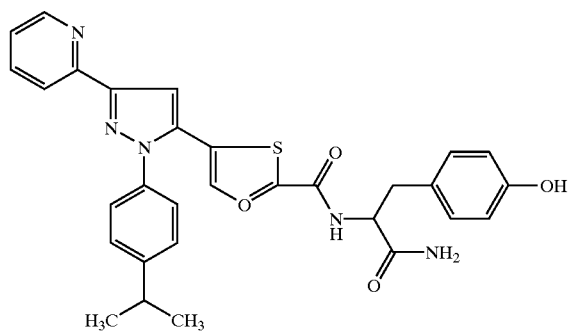
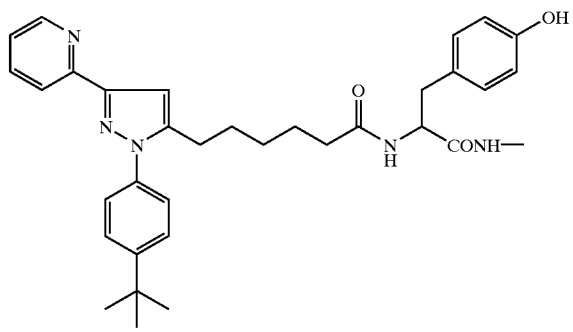
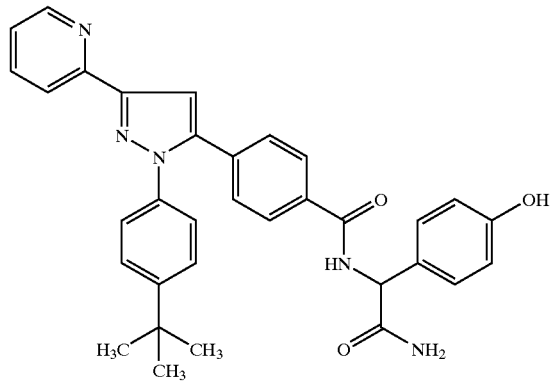
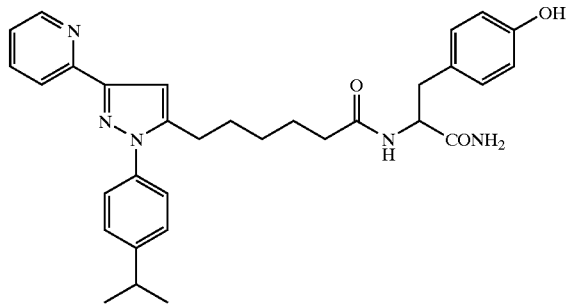
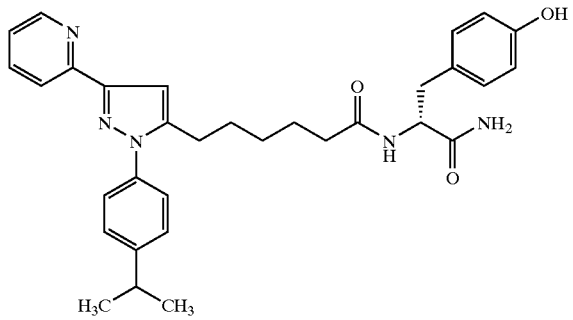
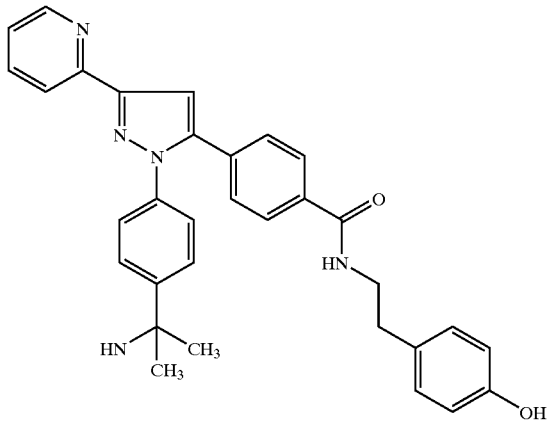

-continued

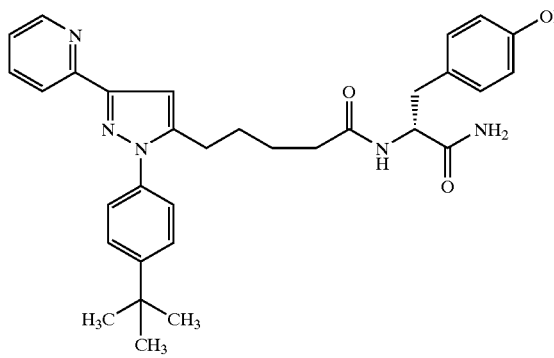

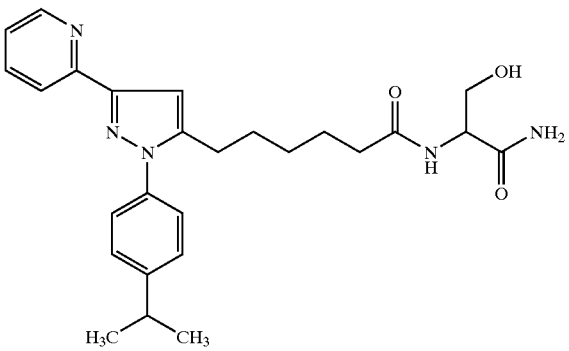

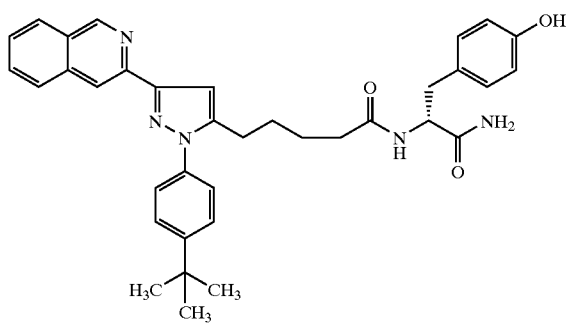

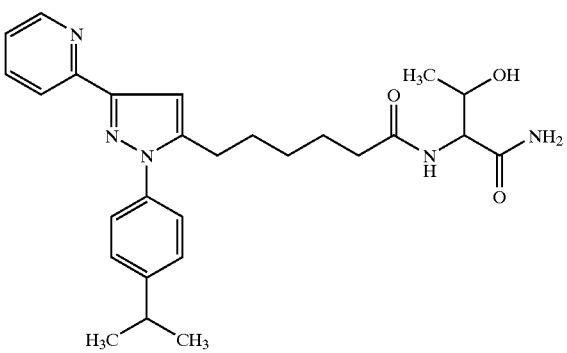

A particularly preferred compound of the invention is the following:

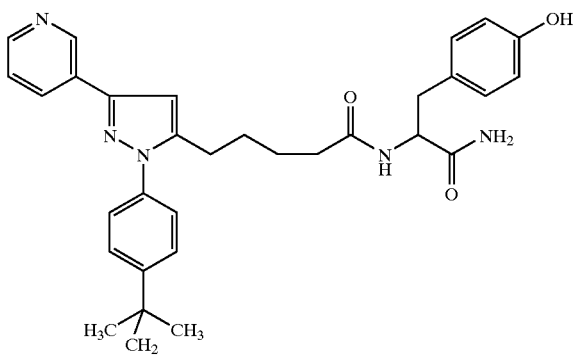

Compounds of the invention can be readily prepared. For instance, substituted pyrazoles suitable as starting reagents are commercially available. Generally preferred are pyrazoles having a 3- and/or 5-position non-hydrogen substituent that can be further functionalized to provide a desired compound of the invention. The pyrazole ring can be readily substituted with desired moieties by known ring addition reactions to provide $R^1$, $R^2$ and $R^3$ substituents. For instance, non-hydrogen $R^2$ and $R^3$ substituents can be provided by Friedel-Crafts-type reactions or Suzuki coupling reactions. See also U.S. Pat. Nos. 5,986,104; 5,744,493; and 5,486,618, for procedures to prepare substituted pyrazoles.

Suitable pyrazoles for use to prepare compounds of the invention also may be readily synthesized. For example, pyrazole reagents may be synthesized by e.g. reaction of a β-dicarbonyl compound with the corresponding substituted hydrazine or the reaction of the dianion of a methyl hydrazone with the corresponding acid chloride or acid anhydride. For extensive description of pyrazoles synthesis, see Handbook of Heterocyclic Chemistry, $2^{nd}$ edition, A. R. Katritzky and A. F. Pozharskii, Pergamon, 2000 or Comprehensive Heterocyclic Chemistry III, A. R. Katritzky, C. W. Rees, E. F. V. Scriven, $1^{st}$ Edition, 1996).

Substituted pyrazole compounds of the invention also may be readily prepared by combinatorial synthetic procedures. For discussions of combinatorial procedures, see, e.g., I. Chaiken et al, *Molecular Diversity and Combinatorial Chemistry*, (ACS, 1996); B. Bunn, *The Combinatorial Index*, (Academic Press 1998). See also A. Marzinzik et al., *Tetrahedron Letters*, 37(7):1003–1006 (1996); Marzinzik et al., *J. Org. Chem.*, 63: 723–727 (1998); and Marzinzik et al: WO 9815532 A1 19980416 for a solid phase combinatorial synthesis of pyrazoles. See also the examples which follow, for exemplary preferred syntheses of pyrazole compounds of the invention.

More particularly, compounds of the invention including specific regioisomers can be suitably prepared by combinatorial synthetic procedures as outlined in the following exemplary Schemes 1, 2 (examples of mixture of isomers) and 3 (as an example of specific regio isomer). It should be appreciated that the compounds shown in the following Schemes are exemplary only, and a variety of other compounds can be employed in a similar manner as described below. Additionally, while in some instances the Schemes detail certain preferred reaction conditions, it will be understood that alternate conditions also may be suitable.

Scheme 1

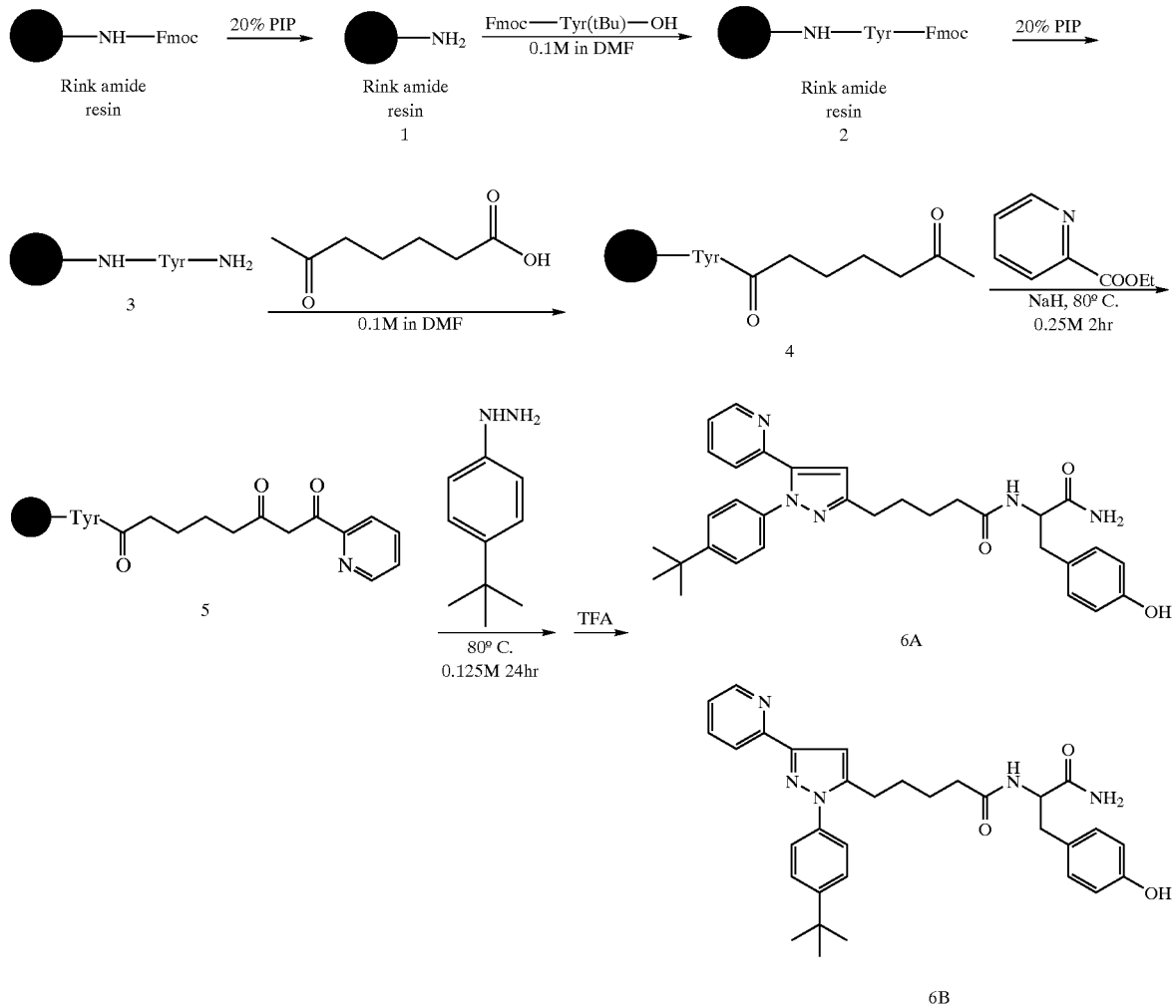

Thus, as depicted in Scheme 1 above, resin bound amine 1 is reacted with a protected amino acid to provide 2 which is reacted with a keto-acid to provide methyl ketone 4. That methyl ketone is reacted with a substituted ester (provides $R^2$ substituent of Formula I) in the presence of strong base to yield the di-ketone 5. The adjacent keto groups with interposed methylene react with a hydrazine to provide the substituted pyrazole as regio isomeric mixtures 6A and 6B.

Scheme 2

-continued

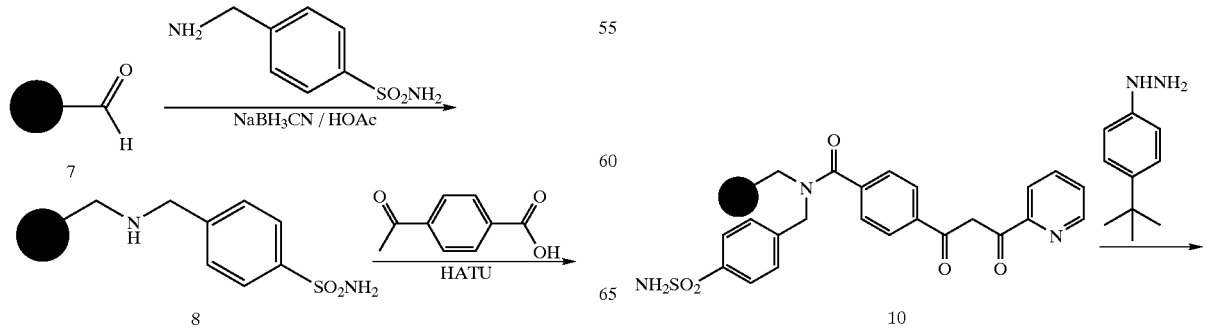

-continued

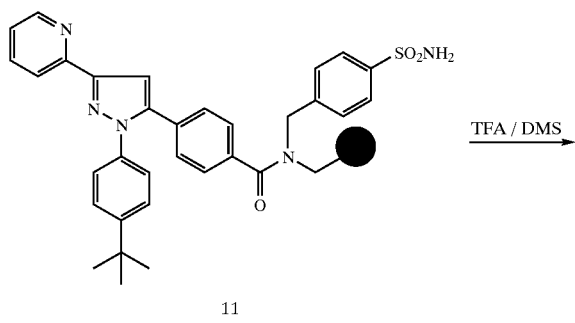

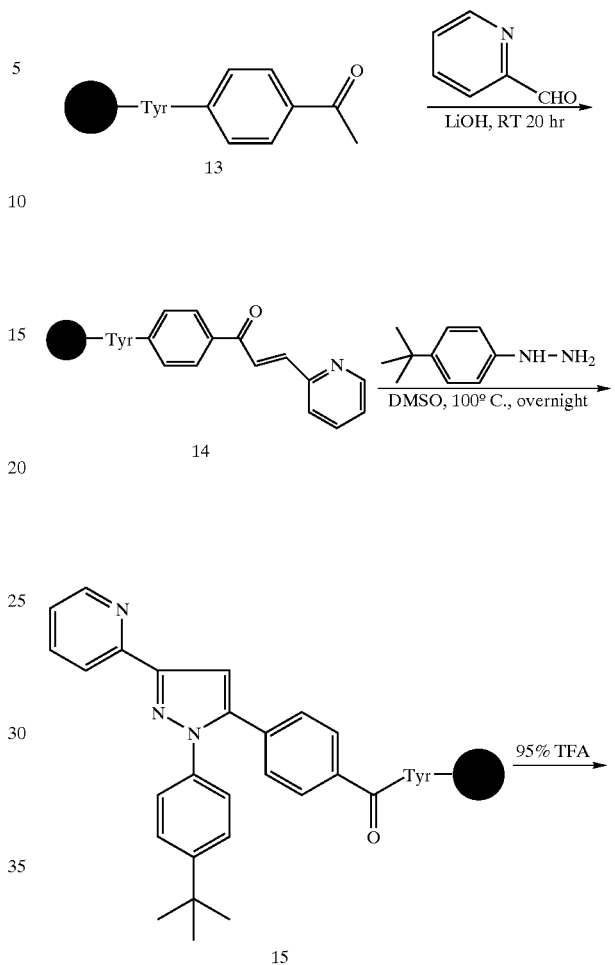

Scheme 2 above depicts another route for combinatorial synthesis of compounds of the invention. Briefly, resin bound aldehyde 7 is functionalized to give secondary amine 8, which is then reacted with a keto-acid to provide tertiary amine 9 with methyl ketone functionality. Reaction with an ester in the presence of a strong base provide compound 10 having adjacent keto groups with interposed methylene that can be reacted with a hydrazine to provide substituted pyrazole 11 and its isomer. Treatment with strong acid releases the pyrazole 12 from the resin.

Scheme 3

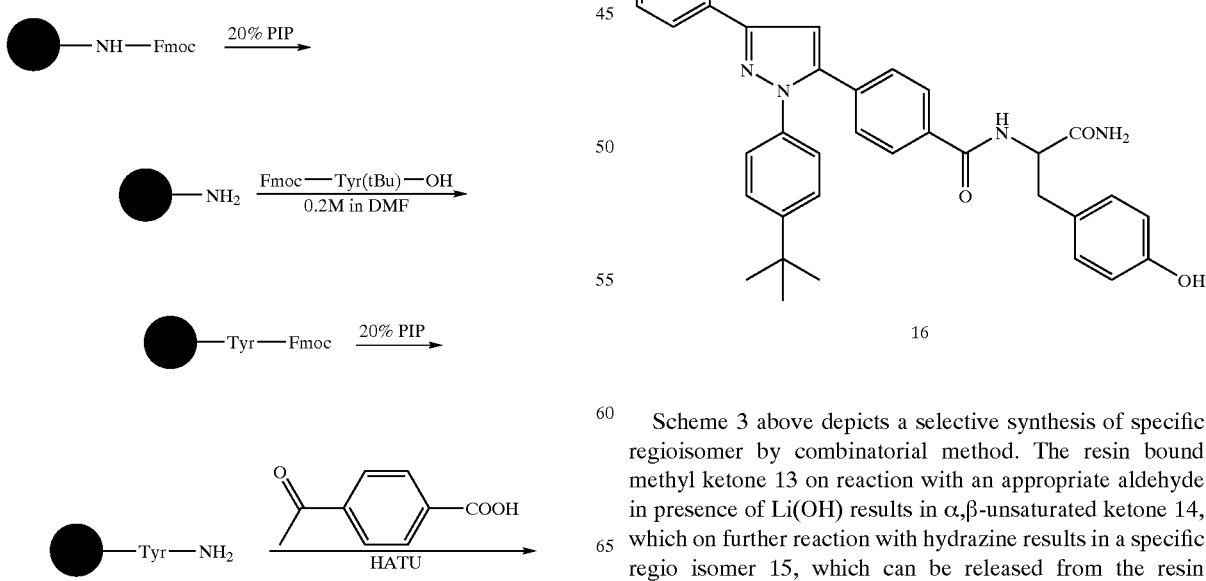

Scheme 3 above depicts a selective synthesis of specific regioisomer by combinatorial method. The resin bound methyl ketone 13 on reaction with an appropriate aldehyde in presence of Li(OH) results in α,β-unsaturated ketone 14, which on further reaction with hydrazine results in a specific regio isomer 15, which can be released from the resin support in the presence of acid to provide pyrazole 16.

Scheme 4

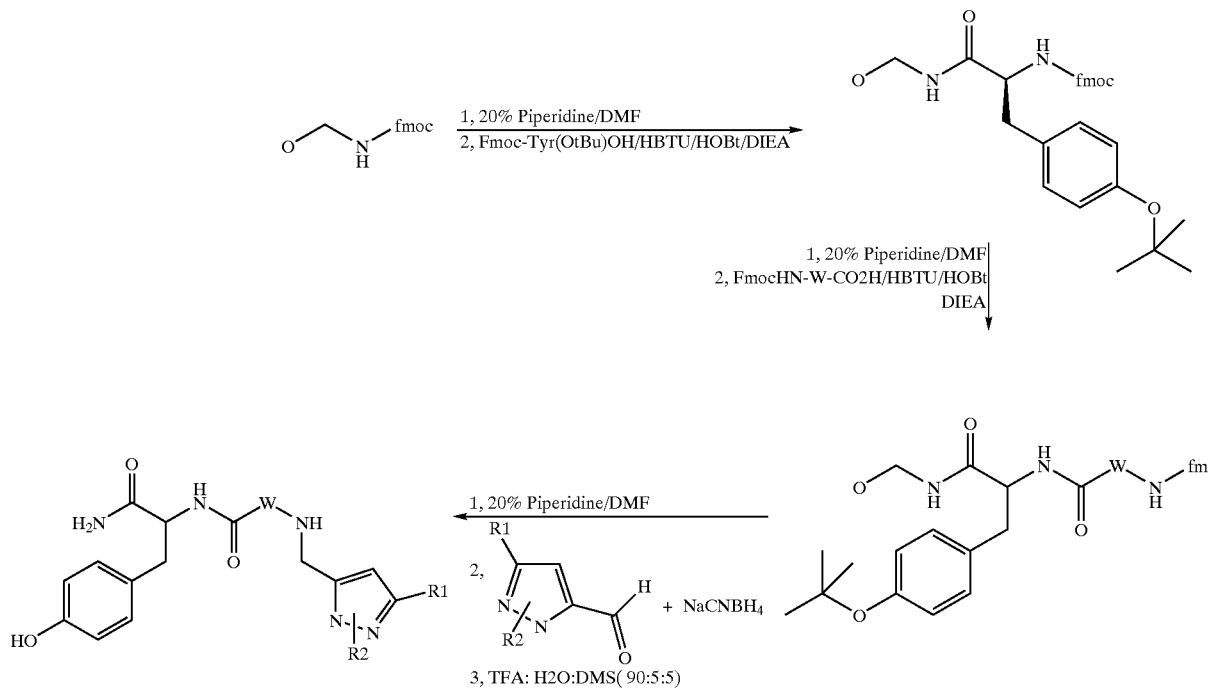

Scheme 4 above depicts the synthesis by combinatorial methods of pyrazole libraries containing a heteroatom on the side chain, particularly compounds of Formulae I, I' and IA where $R^1$ and $R^2$ are as defined above for Formulae I, I', and IA, $R^3$ is H, X is heteroalkylene chain and Y is CO and Z is tyrosine. It should be recognized that while all the reactions shown depict tyro sine as the amino acid (Z=Tyr), by using the appropriate amino acid in the first coupling step other amino acid derivatives may be prepared. In the scheme W is $C_1$–$C_4$ alkyl or 1,3- or 1,4 phenyl radical. All of the reactions shown depict standard coupling reactions which are known to those skilled in the art. The pyrazoles with carboxylic acid or carboxaldehyde in the 3 (or 5) position may be prepared by standard literature procedures as depicted below.

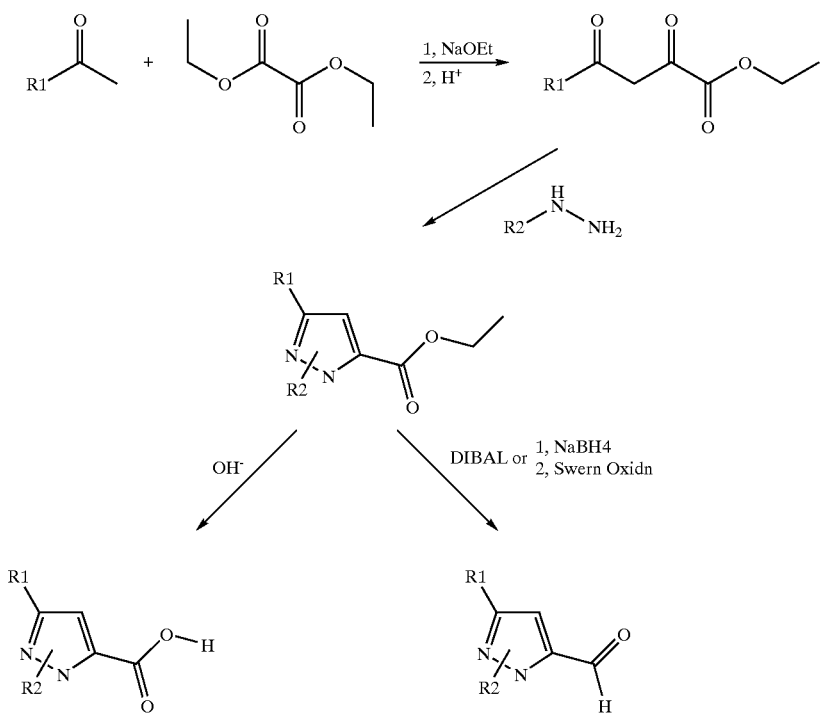

As already mentioned, compounds of the invention including specific regioisomers can be prepared by solution phase synthetic procedures as outlined in the following exemplary Schemes 5 and 6.

derivative 23 where $R^1$ and $R^2$ have the same definition as in Formula I and the appropriate hydrazine. The dianion of the hydrazone is then reacted with an anhydride $(RCO)_2O$ to give the pyrazole 25 where R is $(X)_m—(Y)_n$-Z defined as in

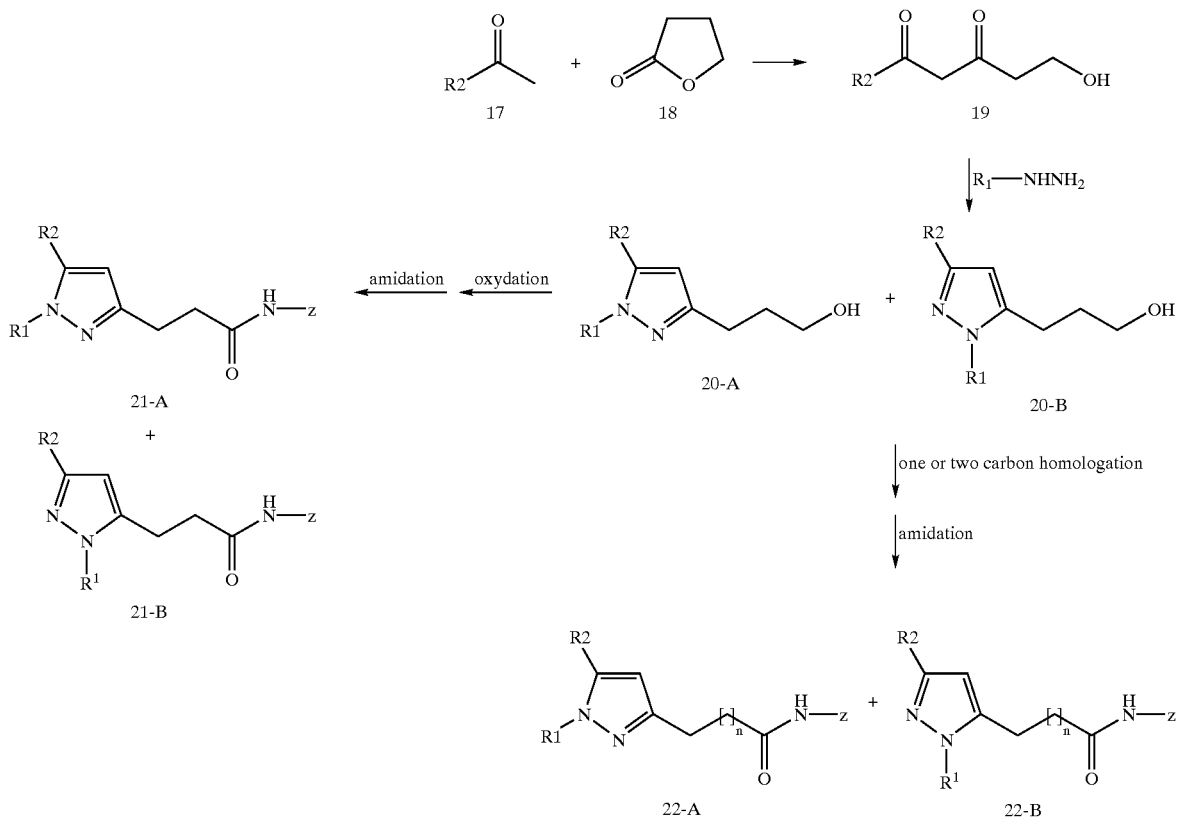

Scheme 5 n = 1–3

Compounds of general formula 20 where $R^1$ and $R^2$ have the same definition as in Formula I can be obtained by reaction of β-diketoalcohol 19 with suitable hydrazine as depicted in scheme 5. This procedure is a preferred one as it gives rise to a better regioselectivity in favor of the 20-B pyrazole regioisomer (see W. V. Murray, Tetrahedron Lett., 34, p.1863, 1993). The hydroxyalkyl pyrazole thus obtained can be oxidized and reacted with an amine or amino-acid $ZNH_2$ where Z is defined as in Formula I using standard amidation conditions (HATU or EDC/HOAT/DIEA for example) to give compounds 21. Homologation by one or two carbons using methods well known to those skilled in the art followed by an amidation step can provide compounds 22.

As an example of such transformation, the hydroxyalkyl derivative 19 can be treated first with iodine in presence of triphenylphosphine and imidazole, then with the anion of tert-butyloxyacetate and finally with trifluoroacetic acid to give the corresponding carboxylic acid. Compounds of formula 22 where n=3 can be obtained from such carboxylic acid by coupling with appropriate amine or amino acid $ZNH_2$ using standard conditions (as HATU or EDC/HOAT/ DIEA).

A second preferred synthetic method for obtaining pyrazoles of the present invention is described in scheme 6. It involves the preparation of hydrazone 24 from an acetyl Formula I or a synthetic precursor which can be easily transformed to $(X)_m—(Y)_n$-Z by methods well known to those skilled in the art. An example of the conditions that can be used for such transformation can be found in S. R. Stauffer, Y. Huang, C. J. Coletta, R. Tedesco, J. A. Katzenellenbogen, Biorg. Med. Chem. 2001, 9, 141–150.

Scheme 6

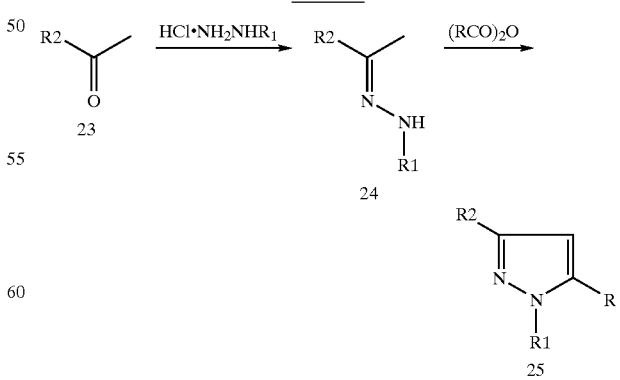

In the case of compounds of Formula IC above, suitable methods for preparation include those exemplified in the following Schemes 7 and 8.

Scheme 7

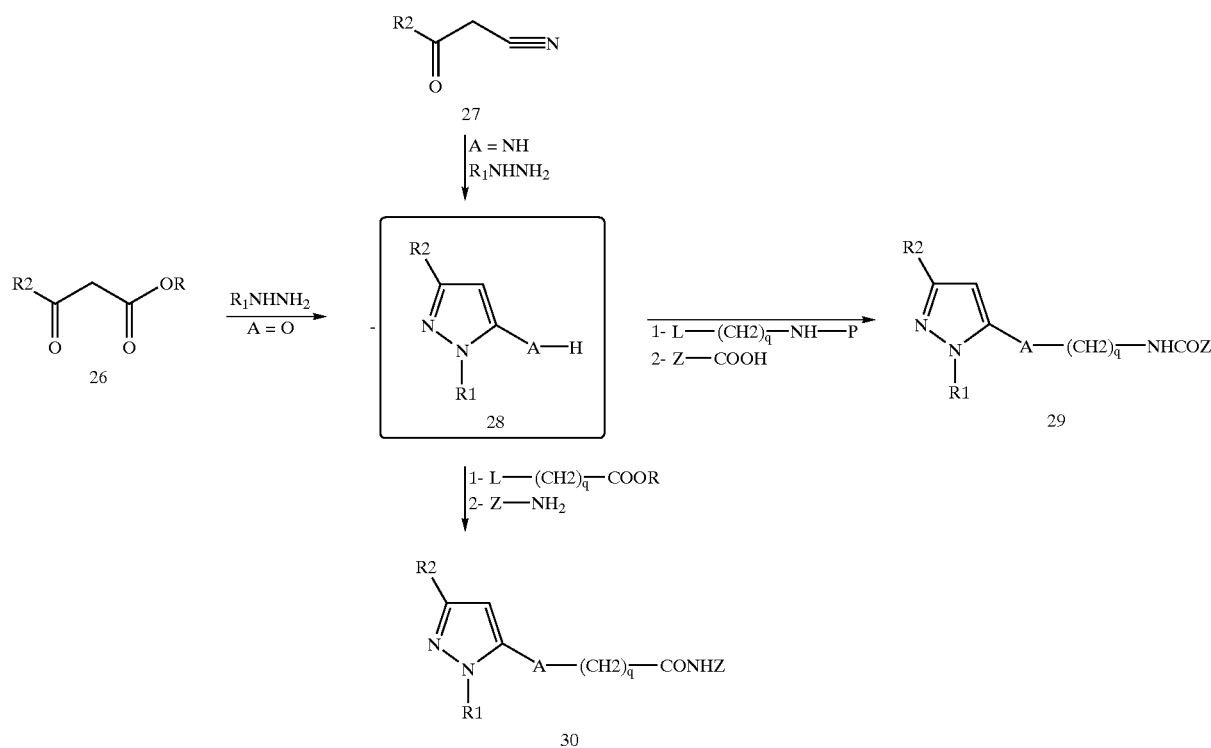

As showed in Scheme 7 above, compounds of general formula 29 and 30 wherein $R^1$, $R^2$ and Z are defined as in Formula I above, A is O or NH and q is a number between 1 and 6, may be obtained by alkylation of an intermediate such as 28 with a reactant such as L-(CH$_2$)q-NH—P wherein L is a leaving group (like OMs, OTs, Cl, Br or I) and P an appropriate protecting group. After appropriate protection/deprotection steps, the intermediate thus obtained can be submitted to standard amidation conditions well known by those skilled in the art. Depending on the nature of A, intermediate 28 can be obtained by reaction with suitable hydrazine $R^1NHNH_2$ either from β-ketoester 26 if A is O or β-keto-nitrile if A is NH. Examples of specific conditions for those reactions can be found in PCT Int. Appl. 9712884 and M. J. Fray, D. J. Bull, M. Kinns, J. Chem. Research (S), p. 11 (1992).

Some compounds of Formula I-C above can be easily obtained from intermediates 20-A and B (see Scheme 5) using synthetic methods well known by those skilled in the art. Scheme 8 below illustrates one of those possible methods yielding to compounds 32-A and B wherein $R^1$, $R^2$ and Z are defined as in Formula I. It should be appreciated that the methods shown in scheme 7 and 8 are exemplary only and that a variety of other methods can be employed to obtained compounds of Formula I–C.

Scheme 8

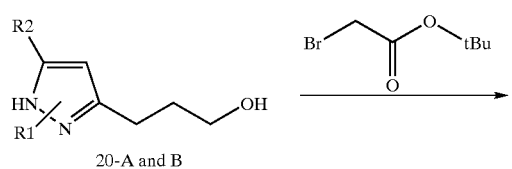

-continued

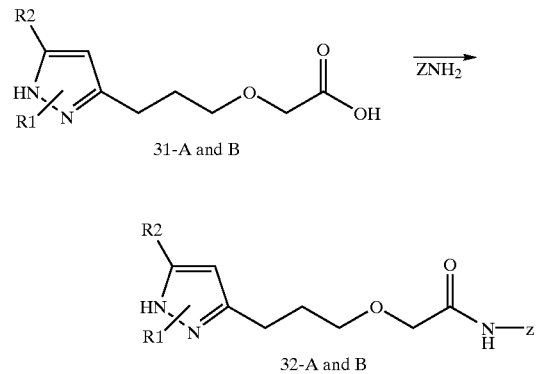

As discussed above, the present invention includes methods for treating infertility in male and female mammals, such as primates, particularly humans. Compounds of the invention will be useful for treatment of infertility conditions currently treated with FSH and/or LH, including female infertility and male spermatogenesis disorders.

The therapeutic methods of the invention generally comprise administration of an effective amount of one or more compounds of the invention to a subject including a mammal, such as a primate, especially a human, in need of such treatment.

Typical candidates for treatment in accordance with the methods of the invention persons suffering from or suspected of suffering from infertility. See the *Merck Manual*, vol. 2, pages 12–17 (16th ed.) for identification of patients suffering from or suspected of infertility, which in the case of humans, can include failure to conceive within one year of unprotected intercourse.

The treatment methods of the invention may be particularly beneficial for female mammals suffering from an ovulatory disorder. Additionally, compounds of the invention can be administered to females undergoing assisted reproductive treatments such as in-vitro fertilization, e.g. to simulate follicular development and maturation. Compounds of the invention also can be administered to males to facilitate adequate spermatogenesis.

The treatment methods of the invention also will be useful for treatment of infertility in mammals other than humans, such as horses and livestock e.g. cattle, sheep, cows and the like.

Compounds of the invention may be administered as a "cocktail" formulation, i.e. coordinated administration of one or more compounds of the invention together with one or more other active therapeutics, particularly one or more other known fertility agents. For instance, one or more compounds of the invention may be administered in coordination with a regime of Follicle Stimulating Hormone and/or Leutinizing Hormone such as Gonal-F, Metrodin HP or Pergonal.

The compounds of this invention can be administered by a variety of routes, such as orally or by injection, e.g., intramuscular, intraperitoneal, subcutaneous or intravenous injection, or topically such as transdermally, vaginally and the like. Compounds of the invention may be suitably administered to a subject in the protonated and water-soluble form, e.g., as a pharmaceutically acceptable salt of an organic or inorganic acid, e.g., hydrochloride, sulfate, hemisulfate, phosphate, nitrate, acetate, oxalate, citrate, maleate, mesylate, etc.

Compounds of the invention can be employed, either alone or in combination with one or more other therapeutic agents as discussed above, as a pharmaceutical composition in mixture with conventional excipient, i.e., pharmaceutically acceptable organic or inorganic carrier substances suitable for oral, parenteral, enteral or topical application which do not deleteriously react with the active compounds and are not deleterious to the recipient thereof. Suitable pharmaceutically acceptable carriers include but are not limited to water, salt solutions, alcohol, vegetable oils, polyethylene glycols, gelatin, lactose, amylose, magnesium stearate, talc, silicic acid, viscous paraffin, perfume oil, fatty acid monoglycerides and diglycerides, petroethral fatty acid esters, hydroxymethyl-cellulose, polyvinylpyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously react with the active compounds.

For oral administration, pharmaceutical compositions containing one or more substituted pyrazole compounds of the invention may be formulated as e.g. tablets, troches, lozenges, aqueous or oily suspensions, dispersible powders or granules, emulsions, hard or soft capsules, syrups, elixers and the like. Typically suitable are tablets, dragees or capsules having talc and/or carbohydrate carrier binder or the like, the carrier preferably being lactose and/or corn starch and/or potato starch. A syrup, elixir or the like can be used wherein a sweetened vehicle is employed. Sustained release compositions can be formulated including those wherein the active component is protected with differentially degradable coatings, e.g., by microencapsulation, multiple coatings, etc.

For parenteral application, e.g., sub-cutaneous, intraperitoneal or intramuscular, particularly suitable are solutions, preferably oily or aqueous solutions as well as suspensions, emulsions, or implants, including suppositories. Ampules are convenient unit dosages.

For topical applications, formulations may be prepared in a topical ointment or cream containing one or more compounds of the invention. When formulated as an ointment, one or more compounds of the invention suitably may be employed with either a paraffinic or a water-miscible base. The one or more compounds also may be formulated with an oil-in-water cream base. Other suitable topical formulations include e.g. lozenges and dermal patches.

It will be appreciated that the actual preferred amounts of active compounds used in a given therapy will vary according to the specific compound being utilized, the particular compositions formulated, the mode of application, the particular site of administration, etc. Optimal administration rates for a given protocol of administration can be readily ascertained by those skilled in the art using conventional dosage determination tests conducted with regard to the foregoing guidelines. See also Remington's Pharmaceutical Sciences. In general, a suitable effective dose of one or more compounds of the invention, particularly when using the more potent compound(s) of the invention, will be in the range of from 0.01 to 100 milligrams per kilogram of bodyweight of recipient per day, preferably in the range of from 0.01 to 20 milligrams per kilogram bodyweight of recipient per day, more preferably in the range of 0.05 to 4 milligrams per kilogram bodyweight of recipient per day. The desired dose is suitably administered once daily, or several sub-doses, e.g. 2 to 4 sub-doses, are administered at appropriate intervals through the day, or other appropriate schedule. Such sub-doses may be administered as unit dosage forms, e.g., containing from 0.05 to 10 milligrams of compound(s) of the invention, per unit dosage.

The entire text of all documents cited herein are incorporated by reference herein. The following non-limiting examples are illustrative of the invention.

EXAMPLE 1

Synthesis of N-(5-[1-(4-tert-butylphenyl)-5-pyridin-3-yl-1H-pyrazol-3-yl]pentanoyl)tyrosinamide (1-A) and N-(5-[1(4-tert-butylphenyl)-3-pyridin-3-yl-1H-pyrazol-5-yl]pentanoyl)tyrosinamide (1-B) on Solid Phase

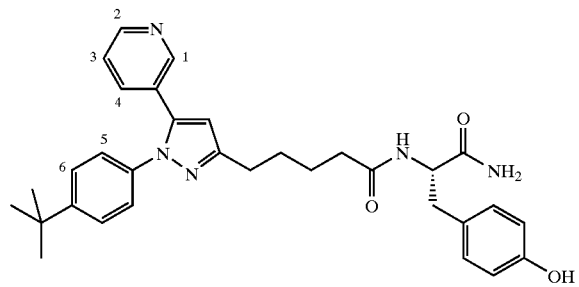

1-A

37

-continued

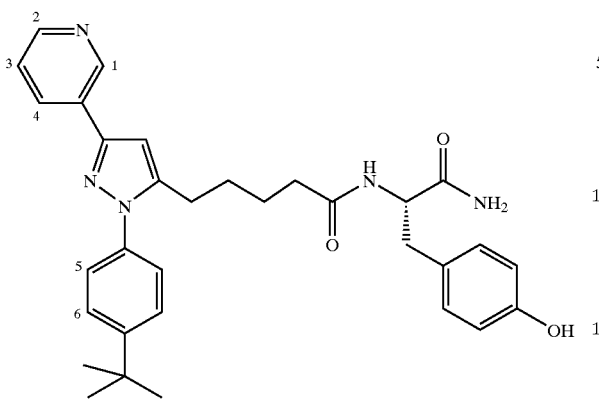

1-B

Rink-amide resin (30 g, loading=0.65mmol/g) was shaken in a large peptide vessel in a 20% piperidine solution in DMF (200 mL) for 30 min. This operation was repeated 2 times. The resin was then washed with DMF (3×), NMP (2×), MeOH (2×) and DCM (2×) and dried under vacuum for 30 min. The deprotected resin was transferred into a 1 L bottle and shaken for 27 h in a solution containing Fmoc—Tyr(tBu)-OH (90 g), HATU (74 g) and DIEA (60 mL) in 360 mL of DMF. After this time, the resin was transferred into a peptide vessel, washed with DMF (3×), DCM (2×), MeOH (2×), DMF (1×), DCM (1×) and dried under vacuum for 15 min. It was then shaken in a 20% piperidine solution in DMF (200 mL) for 30 min 3 times, washed with DMF (3×), NMP (2×), MeOH (2×), DCM (2×) and dried under vacuum for 15 min. For the next step, the resin was transferred again into a 1 L bottle and shaken for 48 h in a solution of acetylvaleric acid (28.1 g), HATU (74.1 g) and DIEA (66 mL) in DMF (360 mL). Same washing procedure as for the preceding coupling step was followed. The resin was dried under vacuum and divided into two portions of about 32 g (portion 1) and 31 g (portion 2).

Portion 1 was transferred into a 1 bottle flushed with nitrogen containing a solution of methylnicotinate (40 g) in 200 mL of DMA. Sodium hydride 95% (70 g) was then added in small portions into the mixture with constant nitrogen flushing. The bottle was placed in an ice bath and agitated by hand until the hydrogen release had stopped. It was then heated at 85° C. for 2 hours with occasional hand agitation. After that time, the mixture was chilled to room temperature and poured slowly into a beaker containing ice and a solution of 15% acetic acid in water. Transfer into a peptide vessel was operated before the standard washing and drying steps. The 18 g of resin thus obtained were poured into a 1 bottle containing 4-tert-butylphenylhhydrazine hydrochloride (39.1 g) and DIEA (33.1 mL) in DMA (360 mL) and heated for 24 hours at 80° C. The bottle was chilled to room temperature and the resin was washed and dried following standard procedure. Finally, it was cleaved with 100 mL of DCM/TFA (2:1) and the residue was concentrated under reduced pressure. It was dissolve in ethyl acetate and washed with slightly basic solution (pH ~8.5–9 obtained with diluted NH$_4$OH). The organic layer was dried over magnesium sulfate, filtered and concentrated to give 3.65 g of crude (yield ~70%). This crude contained a mixture of the two possible pyrazole regioisomers 1A and 1B with a ratio of about 9:1. The two regioisomers were separated by reversed phase HPLC using DELTAPAK C$_{18}$ column with a linear gradient of 0.1% TFA water/acetonitrile 95:5 to 60:40 in one hour.

38

Structures were assigned by Nuclear Overhauser experiments performed on a JEOL 400 MHz NMR apparatus. There were NOE cross peaks displayed between the proton 5 and proton 1 and 4 for isomer A, indicating that the phenyl ring is close from the pyridine ring and no NOE effect observed between those protons for isomer B.

Isomer 1-A (more polar): trifluoroacetate salt of N-(5-[1-(4-tert-butylphenyl)-5-pyridin-3-yl-1H-pyrazol-3-yl]pentanoyl)tyrosinamide $^1$H NMR (DMSO): 1.28 (s, 9H), 1.55 (m, 4H), 2.12 (t, J=7.3 Hz, 2H), 2.63(m, 3H), 2.86 (dd, J=5.3 and 13.9 Hz, 1H), 4.35 (m, 1H), 5.60 (brs, 1H), 6.61 (s, 1H), 6.62 (d, J=8.8 Hz, 2H), 6.98 (m, 1H), 7.01 (d, J=8.8 Hz, 2H), 7.19 (d, J=8.8 Hz, 2H), 7.36 (m, 1H), 7.42 (d, J=8.8 Hz, 2H), 7.51 (dd, J=8.1 and 5.1 Hz, 1H), 7.75 (dt, J=8.1 and 2.2 Hz, 1H), 8.52 (dd, J=2.2 and 0.73 Hz, 1H), 8.58 (dd, J=4.9 and 1.5 Hz, 1H). MS (ESI, pos.): 540 (M+1)

Isomer 1-B (less polar): trifluoroacetate salt of N-(5-[1-(4-tert-butylphenyl)-3-pyridin-3-yl-1H-pyrazol-5-yl]pentanoyl)tyrosinamide $^1$H NMR (DMSO): 1.34 (s, 9H), 1.47 (m, 4H), 2.05 (t, J=9.1 Hz, 2H), 2.61 (m, 1H), 2.64 (t, J=6.9 Hz, 2H), 2.84 (m, 1H), 4.34 (m, 1H), 6.30 (brs, 1H), 6.59 (d, J=8.4 Hz, 2H), 6.98 (m, 1H), 6.99 (d, J=8.4 Hz, 2H), 7.02 (s, 1H), 7.37 (m, 1H), 7.48 (d, J=8.8 Hz, 2H), 7.58 (d, J=8.8 Hz, 2H), 7.86 (d, J=8.4Hz, 1H), 7.92 (dd, J=8.1 and 5.5 Hz, 1H), 8.72 (dt, J=8.4 and 1.46 Hz, 1H), 8.76 (dd, J=5.49 and 1.46 Hz, 1H), 9.24 (d, J=2.2 Hz, 1H). MS (ESI, pos.): 540 (M+1)

EXAMPLE 2

Synthesis of N-(5-[1-(4-tert-butylphenyl)-5-pyridin-4-yl-1H-pyrazol-3-yl]pentanoyl)tyrosinamide (2-A) and N-(5-[1(4-tert-butylphenyl)-3-pyridin-4-yl-1H-pyrazol-5-yl]pentanoyl)tyrosinamide (2-B)

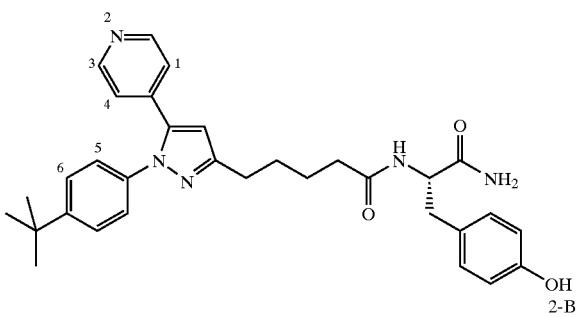

2-A

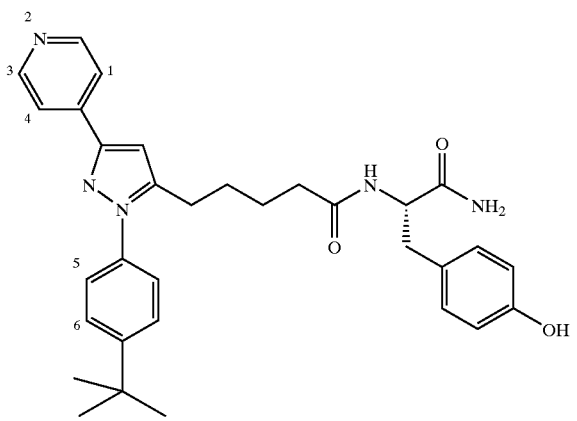

2-B

Those compounds were synthesized from the portion 2 (31 g) of resin obtained in Example 1 above following exactly the same procedure. All the reagents and quantities are the same except that methylnicotinate was replaced by methylisonicotinate.

2.5 g of crude were obtained (48% yield) and contained a mixture of the two possible pyrazole regioisomers 2A and 2B with a ratio of about 9:1. The two regioisomers were separated using the same conditions as those described in example 1. The structures were assigned by analogy with compounds 1A and 1B.

Isomer 2-A (more polar): trifluoroacetate salt of N-(5-[1-(4-tert-butylphenyl)-5-pyridin-4-yl-1H-pyrazol-3-yl]pentanoyl)tyrosinamide $^1$H NMR (DMSO) 1.29 (s, 9H), 1.52 (m, 4H), 2.10 (t, J=7.3Hz, 2H), 2.55 (m, 3H), 2.83 (dd, J=4.4 and 14.3 Hz, 1H), 4.35 (m, 1H), 6.61 (d, J=6.6 Hz, 2H), 6.77 (s, 1H), 7.00 (s, 1H), 7.01 (d, J=6.9 Hz, 2H), 7.22 (d, J=6.6 Hz, 2H), 7.38 (m, 3H), 7.45 (d, J=6.9 Hz, 2H), 7.88 (d, J=8.4 Hz, 1H), 8.63(d, J=4.8 Hz, 2H), 9.2 (brs, 1H). MS (ESI, pos.) : 540 (M+1)

Isomer 2-B (less polar): trifluoroacetate salt of N-(5-[1-(4-tert-butylphenyl)-3-pyridin-4-yl-]H-pyrazol-5-yl]pentanoyl)tyrosinamide $^1$H NMR (DMSO): 1.34 (s, 9H), 1.43 (m, 4H), 2.04 (t, J=9.1 Hz, 2H), 2.50 (m, 1H), 2.64 (m, 2H), 2.83 (dd, J=3.3 and 9.2 Hz,1H), 4.35 (m, 1H), 6.58 (d, J=6.9 Hz, 2H), 6.98 (m, 3H), 7.14 (s, 1H), 7.38 (s, 1H), 7.49 (d, J=6.9 Hz, 2H), 7.59 (d, J=6.9 Hz, 2H), 7.86 (d, J=8.4 Hz, 1H), 8.17 (d, J=4.7 Hz, 2H), 8.78 (d, J=4.1 Hz, 2H), 9.2 (brs, 1H). MS (ESI, pos.): 540 (M+1) Elemental analysis: $C_{32}H_{37}N_5O_3$.TFA.1,5$H_2O$, theoretical: C, 59.99%; H, 6.07%; N, 10.29%; experimental: C, 60.12%; H, 5.95%: N, 10.27%.

EXAMPLE 3

Combinatorial Synthesis of Pyrazole Library of the Invention

A library of ~2500 pyrazoles synthesized via Fmoc/t-Butyl chemistry using either IRORI AccuTag/Robin technology. 20 microkans each in three glass bottles containing Fmoc Rink Amide MBHA resin (25 mg, 0.59 mmol/g) were treated with 20% piperidine/DMF (30 mL, 3×30 min) and then rinsed with DMF and acylated with 0.1 M solution of Fmoc amino acid (3 mmlol) in DMF (30 mL), HATU (3 mmol) and DIEA (6 mmol) at room temperature for 16 hours, rinsed with DMF. Fmoc was removed with 20% piperidine/DMF (100 mL, 3×30 min), rinsed with DMF. 30 microkans in two glass bottles resin were acylated with 0.1 M solution of acetyl carboxylic acid (4.5 mmol) in DMF (45 mL), HATU (4.5 mmol) and DIEA (9 mmol) at room temperature for 16 hours and then rinsed with DMF. Claisen condensation was carried out with 30 microkans in two glass bottles with 0.25 M solution of ester (11.25 mmol), 95% NaH (11.25 mmol) in DMA at 90° C. in the oven for 2 hours. The microkans were washed (DMA, MeOH, DMF and $CH_2Cl_2$) and dried under reduced pressure. Cyclization was carried out with 12 microkans in 5 glass bottles with 0.125M solution of hydrazine (2.25 mmol), DIEA (2.25 mmol) in DMA (18 mL) at 80° C. in the oven for 24 hours, rinsed and dried under reduced pressure. The final cleavage of resin was carried out with TFA at 2 hours in the IRORI cleavage block. The residue was then co-evaporated with $CH_3CN$ under reduced pressure.

All of the crude pyrazoles were analyzed by reversed phase HPLC using DELTAPAK $C_{18}$, 5 μM column, eluted with a linear gradient of 0.1% TFA in $CH_3CN$/water (0% $CH_3CN$/100% water) to 0.1% TFA in $CH_3CN$/water (100% $CH_3CN$/0% water) over a 30 minute period with flow rate of 1.5 mL/minute. The purity of the samples were determined and were essentially found to contain the pyrazole in 60% purity as a mixture of regioisomers. The mass were confirmed by matrix-assisted laser desorption ionization time of flight mass spectral analysis (MALDI-TOF, PE Biosystem, Inc.). Generally the pyrazoles gave the mass of MH+ or M+Na+ or within experimental error of the calculated value.

EXAMPLE 4

Compound Purification

The crude pyrazoles prepared in Example 3 above were purified by reversed phase HPLC using DELTAPAK $C_{18}$, 5 μM column, eluted with a linear gradient of 0.1% TFA in $CH_3CN$/water (0% $CH_3CN$/100% water) to 0.1% TFA in $CH_3CN$/water (100% $CH_3CN$/0% water) over a 30 minute period with flow rate of 15 mL/minute. The purity of the samples were determined and were essentially found to contain one component. The mass were confirmed by matrix-assisted laser desorption ionization time of flight mass spectral analysis (MALDI-TOF, PE Biosystem, Inc.). Generally the pyrazoles gave the mass of MH+ or M+Na+ or within experimental error of the calculated value.

For example, the following compounds were prepared by this procedure:

N-{5-[1-(4-tert-butylphenyl)-3-pyridin-2-yl-1H-pyrazol-5-yl]pentanoyl}tyrosinamide, [M+H]=540;

N-{5-[1-(4-tert-butylphenyl)-3-pyridin-3-yl-1H-pyrazol-5-yl]pentanoyl}tyrosinamide, [M+H]=540;

N-{5-[1-(4-tert-butylphenyl)-5-pyridin-3-yl-1H-pyrazol-3-yl]pentanoyl}tyrosinamide, [M+H]=540;

N-{5-[1-(4-tert-butylphenyl)-3-pyridin-4-yl-1H-pyrazol-5-yl]pentanoyl}tyrosinamide, [M+H]=540;

N-{5-[1-(4-tert-butylphenyl)-5-pyridin-4-yl-1H-pyrazol-3-yl]pentanoyl}tyrosinamide, [M+H]=540;

N-{5-[1-(4-tert-butylphenyl)-3-pyridin-3-yl-1H-pyrazol-5-yl]pentanoyl}-N,N-dimethyltyrosinamide, [M+H]=554;

N-[4-(1-butyl-3-isoquinolin-3-yl-1H-pyrazol-5-yl)benzoyl]tyrosinamide, [M+H]=534;

N-{5-[1-(4-isopropylphenyl)-3-pyridin-3-yl-1H-pyrazol-5-yl]pentanoyl}tyrosinamide, [M+H]=526;

N-{6-[1-(4-isopropylphenyl)-3-pyridin-2-yl-1H-pyrazol-5-yl]hexanoyl}tyrosinamide, [M+H]=540;

N-{6-[1-(4-tert-butylphenyl)-3-pyridin-2-yl-1H-pyrazol-5-yl]hexanoyl}-3-hydroxyphenylalaninamide, [M+H]=554;

N-[1-(aminocarbonyl)-3-(4-hydroxyphenyl)propyl]-5-[1-(4-tert-butylphenyl)-3-pyridin-2-yl-1H-pyrazol-5-yl]pentanamide, [M+H]=554;

N-[5-(1-butyl-3-isoquinolin-3-yl-1H-pyrazol-5-yl)pentanoyl]tyrosinamide, [M+H]=514;

N-{6-[1-(4-tert-butylphenyl)-3-pyridin-2-yl-1H-pyrazol-5-yl]hexanoyl}serinamide, [M+H]=478;

N-{6-[1-(4-iso-propylphenyl)-3-pyridin-2-yl-1H-pyrazol-5-yl]hexanoyl}serinamide, [M+H]464;

N-{6-[1-(4-iso-propylphenyl)-3-pyridin-2-yl-1H-pyrazol-5-yl]hexanoyl}threonamide, [M+H]=478;

N-{5-[1-(4-isopropylphenyl)-3-pyridin-2-yl-1H-pyrazol-5-yl]pentanoyl}tyrosinamide, [M+H]=526;

6-[1-(4-tert-butylphenyl)-3-pyridin-2-yl-1H-pyrazol-5-yl]-N-[2-(4-hydroxyphenyl)ethyl]hexanamide, [M+H]=511;

N-{6-[1-(4-tert-butylphenyl)-3-pyridin-2-yl-1H-pyrazol-5-yl]hexanoyl}tyrosinamide, [M+H]=554;

N-{5-[1-(4-tert-butylphenyl)-3-isoquinolin-3-yl-1H-pyrazol-5-yl]pentanoyl}tyrosinamide, [M+H]=590;

N-{6-[1-(4-tert-butylphenyl)-3-isoquinolin-3-yl-1H-pyrazol-5-yl]hexanoyl}tyrosinamide, [M+H]=604;
N-{6-[1-(4-tert-butylphenyl)-3-pyridin-2-yl-1H-pyrazol-5-yl]hexanoyl}-N-methyltyrosinamide, [M+H]=568;
N-{6-[1-(4-tert-butylphenyl)-3-pyridin-2-yl-1H-pyrazol-5-yl]hexanoyl}-4-(hydroxymethyl)phenylalaninamide, [M+H]=568;
4-amino-N-{6-[1-(4-tert-butylphenyl)-3-pyridin-2-yl-1H-pyrazol-5-yl]hexanoyl}phenylalaninamide, [M+H]=553;
4-(acetylamino)-N-{6-[1-(4-tert-butylphenyl)-3-pyridin-2-yl-1H-pyrazol-5-yl]hexanoyl}phenylalaninamide, [M+H]=595;
4-(aminocarbonyl)-N-{6-[1-(4-tert-butylphenyl)-3-pyridin-2-yl-1H-pyrazol-5-yl]hexanoyl}phenylalaninamide, [M+H]=581;
N-butyl-N-{6-[1-(4-tert-butylphenyl)-3-pyridin-2-yl-1H-pyrazol-5-yl]hexanoyl}tyrosinamide, [M+H]=610;
N-{6-[1-(4-tert-butylphenyl)-3-pyridin-2-yl-1H-pyrazol-5-yl]hexanoyl}threonamide, [M+H]=492;
N-[2-amino-1-(4-hydroxyphenyl)-2-oxoethyl]-6-[1-4-tert-butylphenyl)-3-pyridin-2-yl-1H-pyrazol-5-yl]hexanamide, [M+H]=540;
N-{2-[4-(aminosulfonyl)phenyl]ethyl}-5-[1-(4-tert-butylphenyl)-3-pyridin-2-yl-1H-5-yl]pentanamide, [M+H]=560;
N-({5-[1-(4-isopropylphenyl)-3-pyridin-2-yl-1H-pyrazol-5-yl]thien-2-yl}carbonyl)tyrosinamide, [M+H]=552;
N-[2-amino-1-(4-hydroxyphenyl)-2-oxoethyl]-4-[1-(4-tert-butylphenyl)-3-pyridin-2-yl-1H-pyrazol-5-yl]benzamide, [M+H]=546;
4-[1-(4-tert-butylphenyl)-3-pyridin-2-yl-1H-pyrazol-5-yl]-N-[2-(4-hydroxyphenyl)ethyl]benzamide, [M+H]=517;
N-{3-[1-(4-tert-butylbenzyl)-3-isoquinolin-3-yl-1H-pyrazol-5-yl]benzoyl}tyrosinamide, [M+H]=608;
N-{5-[1-(4-tert-butylphenyl)-3-pyridin-4-yl-1H-pyrazol-5-yl]pentanoyl}tyrosinamide, [M+H]=540;
N-{3-[1-(4-tert-butylbenzyl)-3-pyridin-3-yl-1H-pyrazol-5-yl]benzoyl}tyrosinamide, [M+H]=574;
N-{3-[1-(4-tert-butylphenyl)-3-isoquinolin-3-yl-1H-pyrazol-5-yl]benzoyl}tyrosinamide, [M+H]=610;
N-[4-(1-butyl-3-isoquinolin-3-yl-1H-pyrazol-5-yl)benzoyl]tyrosinamide, [M+H]=534;
N-{3-[1-(4-tert-butylbenzyl)-3-quinolin-3-yl-1H-pyrazol-5-yl]benzoyl}tyrosinamide, [M+H]=624;
N-{3-[3-isoquinolin-3-yl-1-(4-propylphenyl)-1H-pyrazol-5-yl]benzoyl}tyrosinamide, [M+H]=610;
N-{3-[1-(4-tert-butylphenyl)-3-pyridin-3-yl-1H-pyrazol-5-yl]benzoyl}tyrosinamide, [M+H]=560;
N-{4-[1-4-tert-butylphenyl)-3-pyridin-3-yl-1H-pyrazol-5-yl]benzoyl}tyrosinamide, [M+H]=560;
N-{5-[1-(4-tert-butylbenzyl)-3-pyridin-4-yl-1H-pyrazol-5-yl]pentanoyl}tyrosinamide, [M+H]=554;
N-{3-[1-(4-tert-butylbenzyl)-3-pyridin-4-yl-1H-pyrazol-5-yl]benzoyl}tyrosinamide, [M+H]=574;
N-{5-[1-(4-tert-butylbenzyl)-3-pyridin-3-yl-1H-pyrazol-5-l]pentanoyl}tyrosinamide, [M+H]=554;
N-[3-(1-butyl-3-isoquinolin-3-yl-1H-pyrazol-5-yl)benzoyl]tyrosinamide, [M+H]=534;
N-{4-[1-butyl-3-(2-furyl)-1H-pyrazol-5-yl]benzoyl}tyrosinamide, {M+H]=473;
N-{5-[1-butyl-3-(2-furyl)-1H-pyrazol-5-yl]pentanoyl}tyrosinamide, [M+H]=453;
N-{3-[3-(2-furyl)-1-(4-isopropylphenyl)-1H-pyrazol-5-yl]propanoyl}tyrosinamide, {M+H]=487;
N-(4-{1-(4-tert-butylphenyl)-3-[3-(dimethylamino)phenyl]-1H-pyrazol-5-yl}benzoyl)tyrosinamide, [M+H]=602;
N-[1-(aminocarbonyl)-3-(4-hydroxyphenyl)propyl]-4-[3-(2-furyl)-1-(4-isopropylphenyl)-1H-pyrazol-5-yl]benzamide, [M+H]549;

N-[1-(aminocarbonyl)-3-(4-hydroxyphenyl)propyl]-5-{1-(4-tert-butylphenyl)-3-[3-(dimethylamino)phenyl]-1H-pyrazol-5-yl}pentanamide, [M+H]596;
N-{5-[1-(4-tert-butylphenyl)-3-(2-furyl)-1H-pyrazol-5-yl]pentanoyl}tyrosinamide, [M+H]=529;
N-[1-(aminocarbonyl)-3-(4-hydroxyphenyl)propyl]-4-[3-(2-furyl)-1-pyridin-2-yl-1H-pyrazol-5-yl]benzamide, [M+H]=508;
N-(4-{3-[3-(dimethylamino)phenyl]-1-pyridin-2-yl-1H-pyrazol-5-yl}benzoyl)tyrosinamide, [M+H]=547;
N-(5-{1-butyl-3-[3-(dimethylamino)phenyl]-1H-pyrazol-5-yl}pentanoyl)tyrosinamide, [M+H]=506;
N-(5-{1-(4-tert-butylphenyl)-3-[3-(dimethylamino)phenyl]-1H-pyrazol-5-yl}pentanoyl)tyrosinamide, [M+H]=582;
N-[5-(1-butyl-3-quinolin-3-yl-1H-pyrazol-5-yl)pentanoyl]tyrosinamide, [M+H]=514;
N-{5-[1-(4-tert-butylphenyl)-3-quinolin-3-yl-1H-pyrazol-5-yl]pentanoyl}tyrosinamide, [M+H}=590;
N-[5-(1-butyl-3-quinolin-6-yl-1H-pyrazol-5-yl)pentanoyl]tyrosinamide, [M+H]=514;
N-{5-[1-(4-tert-butylphenyl)-3-quinolin-6-yl-1H-pyrazol-5-yl]pentanoyl}tyrosinamide, [M+H]=590;
N-{5-[1-(4-tert-butylbenzyl)-3-quinolin-6-yl-1H-pyrazol-5-yl]pentanoyl}tyrosinamide, [M+H]=604;
N-[5-(1-hexyl-3-pyrazin-2-yl-1H-pyrazol-5-yl)pentanoyl]tyrosinamide, [M+H]=493;
N-[(1-butyl-3-pyridin-3-yl-1H-pyrazol-5-yl)methyl]glycyltyrosinamide; [M+H]=451;
N-{[1-(4-tert-butylphenyl)-3-pyridin-3-yl-1H-pyrazol-5-yl]methyl}glycyltyrosinamide, [M+H]=527;
N-[(1-butyl-3-pyridin-3-yl-1H-pyrazol-5-yl)methyl]-beta-alanyltyrosinamide, [M+H]=465;
N-(3-{[(1-butyl-3-pyridin-3-yl-1H-pyrazol-5-yl)methyl]amino}benzoyl)tyrosinamide, [M+H]=513;
N-[[3-({[1-(4-tert-butylphenyl)-3-pyridin-4-yl-1H-pyrazol-5-yl]methyl}amino)benzoyl]tyrosinamide, [M+H]=589;
N-({1-[(1-butyl-3-pyridin-3-yl-1H-pyrazol-5-yl)methyl]piperidin-4-yl}carbonyl)tyrosinamide, [M+H]505;
N-[(1-{[1-(4-tert-butylphenyl)-3-pyridin-3-yl-1H-pyrazol-5-yl]methyl}piperidin-4-yl)carbonyl]tyrosinamide, [M+H]=581;
N-2--{[1-(4-tert-butylphenyl)-3-pyridin-3-yl-1H-pyrazol-5-yl]methyl}-N~1~-[2-(4-hydroxyphenyl)ethyl]glycinamide; [M+H]=484;
N-3-[(1-butyl-3-pyridin-3-yl-1H-pyrazol-5-yl)methyl]-N~1~-[2-(4-hydroxyphenyl)ethyl]-beta-alaninamide, [M+H]=422;
4-{[(1-butyl-3-pyridin-3-yl-1H-pyrazol-5-yl)methyl]amino}-N-[2-(4-hydroxyphenyl)ethyl]benzamide, [M+H]=470.

EXAMPLE 5

Regioselective Synthesis of Pyrazoles

Commercially available Fmoc-protected rink amide resin (0.7 g) was deprotected with 20% piperidine in DMF, rinsed and acylated with 0.5M solution of Fmoc-amino acid (10 equiv)/HATU (10 equiv)/DIEA (20 equiv) overnight in DMF at room temperature, rinsed with DMF. Fmoc group was removed with 20% piperidine/DMF and resin was rinsed with DMF, acylated with 0.5M solution of acetyl carboxylic acid (10 equiv)/HATU (10 equiv)/DIEA (20 equiv) overnight at room temperature, rinsed with DMF. The resin was added with LiOH.H2O (40 equivalents) in anhydrous DME and 40 equivalents of aldehyde was added. The resin was shaken for 16 hrs and filtered and washed with glacial acetic acid, DMA, I-PrOH, DCM. The resulted α,β-unsaturated ketone was cyclized to pyrazole by adding the 0.5M solution of 4-t-butyl phenyl hydrazine in DMSO and allowing the reaction to proceed for 16 hrs. Resin was washed with DMA, i-PrOH, DCM and dried before treating with TFA release the desired pyrazole product from the resin. The crude product was purified by preparative HPLC.

EXAMPLE 6

Solution Phase Synthesis

Synthesis of N-(3-[1-(4-tert-butylphenyl)-5-pyridin-3-yl-1H-pyrazol-3-yl]propanoyl)tyrosinamide (3-A) and N-(3-[1-(4-tert-butylphenyl)-3-pyridin-3-yl-1H-pyrazol-5-yl]propanoyl)tyrosinamide (3-B)

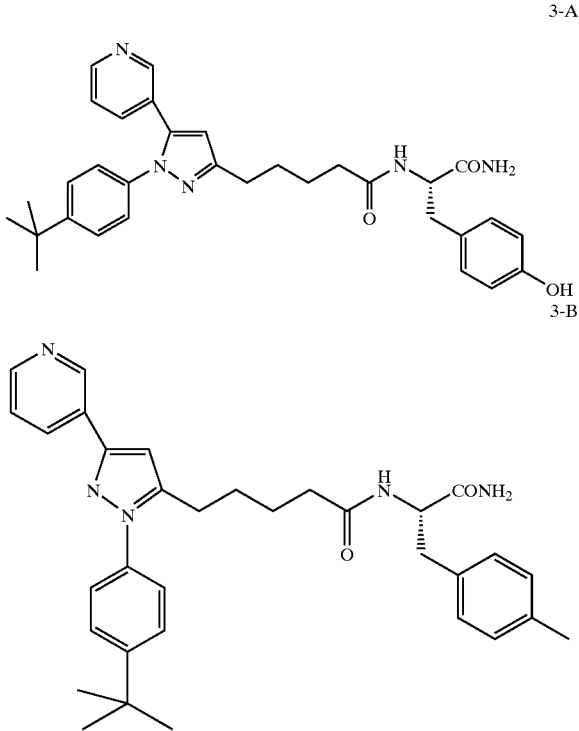

Compound 3-A: 6-Hydroxy-1-(3-pyridinyl)-hexan-1,3-dione

A solution of γ-butyrolactone (1.92 mL, 2.15 g, 25.0 mmol), 60% suspension of sodium hydride in mineral oil (300 mg, 7.50 mmol) and 3-acetylpyridine (551 µL, 606 mg, 5.00 mmol) in dimethylsulfoxyde (4 mL) and tetrahydrofuran (36 mL) was stirred overnight at 25° C. Ethanol (4 mL) was added to destroy excess sodium hydride and the reaction mixture was adsorbed on silica gel (10 g). Flash chromatography on silica gel (75 g), eluting with DCM/MeOH/NH$_4$OH (96/4/1), gave 1.14 g of a yellow oil containing compound 3-A (0.62 g, 60%).

$^1$H NMR (CDCl$_3$): δ 9.00 (d, J=1.8 Hz, 1H), 8.65 (dd, J=4.8, 1.5 Hz, 1H), 8.09 (dt, J=8.1, 2.2 Hz, 1H), 7.34 (dd, J=8.1, 4.8 Hz, 1H), 6.17 (s, 1H), 3.64 (t, J=6.2, 2H), 2.5 (m, 2H), 1.88 (t, J=6.2, 2H). MS (ESI, +): 208 (M+1)

Compound 3-B: 3-{1-(4-tert-butylphenyl)-5-pyridin-3-yl-1H-pyrazol-3-yl}propan-1-ol and 3-{1-(4-tert-butylphenyl)-3-pyridin-3-yl-1H-pyrazol-5-yl}propan-1-ol.

A solution of compound 3-A (370 mg, 1.79 mmol) and 4-tert-butylphenylhydrazine hydrochloride (359 mg, 1.79 mmol) in absolute methanol (10 mL) was stirred overnight at 25° C. The reaction mixture was then adsorbed on silica gel (5 g) and purified by flash chromatography on silica gel (60 g), eluting with DCM/MeOH/NH$_4$OH (96/4/1), to afford 709 mg of a yellow oil containing the pyrazole 3-B (two regioisomers, 452 mg, 75%, ratio 24/76) and DMSO. An aliquot of this mixture was purified with preparative HPLC deltapack C18 column, using a gradient of water/acetonitrile from 95/5 to 50/50 in 60 min, to give pure samples of the two regioisomers.

More Polar Regioisomer:

$^1$H NMR (CDCl$_3$): δ 8.80 (s, 1H), 8.76 (d, J=5.0 Hz, 1H), 7.95 (d, J=8.1), 7.70 (dd, J=8.1, 5.4 Hz, 1H), 7.43 (d, J=7.7 Hz, 2H), 7.16 (d, J=8.1 Hz, 2H),6.60 (s, 1H), 4.48 (t, J=6.0 Hz, 2H), 2.88 (t, J=7.3 Hz, 2H), 2.23(pent., J=7.0 Hz, 2H), 1.32 (s, 9H). MS (ESI, +): 336 (M+1)

Less Polar Regioisomer (Partially Salified with Trifluoroacetate):

$^1$H NMR (CDCl$_3$): δ 9.30 (d, J=9.2 Hz, 1H), 8.87 (d, J=8.4 Hz, 1H), 8.73 (t, J=5.8 Hz, 1H), 7.9 (m, 1H), 7.5 (m, 2H), 7.3 (m, 2H), 6.81 (s, 0.6H), 6.77 (s, 0.4H), 4.36 (t, J=6.0 Hz, 1.2H), 3.71 (t, J=6.0 Hz, 0.8H),2.83(t, J=7.7 Hz, 1.2H), 2.81 (t, J=8.0 Hz), 2.10 (pent., J=7.7 Hz, 1.2H), 1.92 (pent., J=7.3 Hz, 0.8H), 1.36 (s, 9H). MS (ESI, +): 336 (M+1)

Compound 3-C: 3-{1-(4-tert-butylphenyl)-5-pyridin-3-yl-1H-pyrazol-3-yl}propanoic acid and 3-{1-(4-tert-butylphenyl)-3-pyridin-3-yl-1H-pyrazol-5-yl}propanoic acid To a solution of pyrazoles 3-B (168 mg, 0.500 mmol) in acetone (4 mL) was added a solution of 2N H$_2$Cr$_2$O$_7$ (0.75 mL) at 10° C. The mixture was stirred for 1 h, and the solution was decanted away from solid, concentrated and filtrated through a C$_{18}$ column with a mixture 95/5 of water/acetonitrile. Once concentrated, the residue was engaged directly into the next step.

MS (ESI, +): 350 (M+1)

Compound 3: N-(3-[1-(4-tert-butylphenyl)-5-pyridin-3-yl-1H-pyrazol-3-yl]propanoyl)tyrosinamide (3-A) and N-(3-[1-(4-tert-butylphenyl)-3-pyridin-3-yl-1H-pyrazol-5-yl]propanoyl)tyrosinamide (3-B)

To a solution of compounds 3-C (150 mg, 0.43 mmol), 1-ethyl-3-(3'-dimethylaminopropyl)carbodiimide hydrochloride (104 mg, 0.54 mmol), HOAT (73 mg, 0.54 mmol) and N,N-diisopropylethylamine (229 µL, 174 mg, 1.35 mmol) in N,N-dimethylformamide (3 mL) was added O-(tert-butyl)tyrosinamide (128 mg, 0.54 mmol). The reaction mixture was stirred overnight at 25° C., then diluted with a solution of 0.1N ammonia (30 mL) and extracted with ethyl acetate (3×25 mL). The combined organic phases are dried over magnesium sulfate, filtrated and concentrated. The crude thus obtained was dissolved in dichloromethane (5 mL) and stirred overnight at room temperature in presence of trifluoroacetic acid (2 mL). The reaction mixture was concentrated and injected on HPLC deltapack C18 column for purification using a linear gradient of 0.1% TFA water/acetonitrile from 95/5 to 60/40 in 60 min to give the two possible regioisomers whose structures were assigned by analogy with compounds 1-A and 1-B.

N-(3-[1-(4-tert-butylphenyl)-5-pyridin-3-yl-1H-pyrazol-3-yl]propanoyl)tyrosinamide (3-A):

$^1$H NMR (DMSO): δ 8.54 (s, 1H), 8.45 (s, 1H), 8.03 (d, J=8.4 Hz, 1H), 7.66 (d, J=8.1 Hz, 1H), 7.42 (m, 3H), 7.38 (s, 1H), 7.16 (d, J=7.3 Hz, 2H), 7.01 (d, J=8.1 Hz, 2H), 7.00 (s, 1H), 6.61 (d, J=7.0 Hz, 2H), 6.56 (s, 1H), 4.38 (m, 1H), 2.90–2.75 (m 3H), 2.64 (dd, J=13.9, 9.9 Hz, 1H), 2.50 (m, 2H), 1.28 (s, 9H). MS (ESI, +): 512(M+1)

N-(3-[1-(4-tert-butylphenyl)-3-pyridin-3-yl-1H-pyrazol-5-yl]propanoyl)tyrosinamide (3-B) :

$^1$H NMR (DMSO): δ 9.15 (s, 1H), 8.68 (s, 1H), 8.51 (d, J=7.3 Hz, 1H), 8.13 (d, J=8.5 Hz, 1H), 7.76 (m, 1H), 7.58 (d,

J 8.4 Hz, 2H), 7.47 (d, J=8.4 Hz, 2H), 7.44 (s, 1H), 7.02 (s, 1H), 6.99 (d, J=8.4 Hz, 2H), 6.93 (s, 1H), 6.58 (d, J=8.4 Hz, 2H), 3.34 (m, 1H), 2.88–2.79 (m, 3 H), 2.63 (dd, J=14.3, 10.2 Hz, 1H), 2.50 (m, 3H) 1.34 (s, 9H). MS (ESI, +): 512 (M+1)

EXAMPLE 7

Synthesis of the trifluoroacetate salt of N-(4-{[1-(4-tert-butylphenyl)-3-pyridin-4-yl-1H-pyrazol-5-yl]amino}butanoyl)tyrosinamide 7

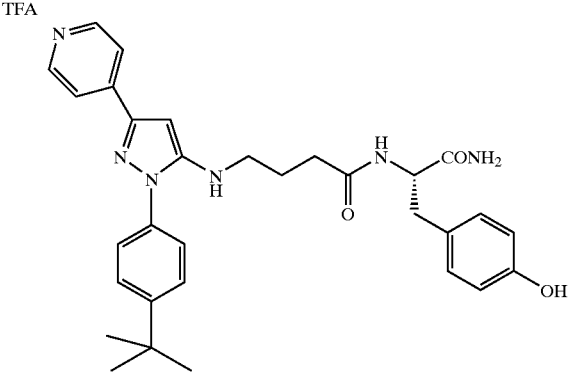

Compound 7a: N-[1-(4-tert-butylphenyl)-3-pyridin-4-yl-1H-pyrazol-5-yl]-trifluoroacetamide N-[1-(4-tert-butylphenyl)-3-pyridin-4-yl-1H-pyrazol-5-yl]-amine (1.05 g, 3.60 mmol) obtained following literature procedure (J. Chem. Research(S), 10, 1992) was dissolved in pyridine, trifluoroacetic anhydride (530 µl, 3.78 mmol) was then slowly added and the mixture was stirred under nitrogen atmosphere at room temperature for 12 h. Pyridine was concentrated under reduced pressure and the resulting brown oil was dissolved in Ethyl acetate and washed twice with water and twice with brine. The organic layer was dried over magnesium sulfate, filtered and concentrated to give 1.17 g of crude material. This crude was purified by flash chromatography with DCM/MeOH/NH$_4$OH (95/5/1 then 85/5/1). 387 mg (yield=28%) of pure material was isolated beside degradations products.

$^1$H NMR (CDCl$_3$): 1.34 (s, 9H), 7.21 (s, 1H), 7.41 (d, J=8.8 Hz, 2H), 7.56 (d, J=8.7 Hz, 2H), 7.72 (m, 2H), 8.47 (m, 1H), 8.58 (m, 2H). MS (ESI, +): 389 (M+1)

Compound 7b: 4-{[1-(4-tert-butylphenyl)-3-pyridin-4-yl-1H-pyrazol-5-yl](trifluoroacetyl)amino}butanoic acid A solution of compound 7a (387 mg, 1.0 mmol) and ethyl-4-bromobutyrate (780 mg, 4 mmol) in acetone (15 mL) was heated under reflux in presence of potassium carbonate (553 mg, 4.0 mmol) and potassium iodide (183 mg, 1.1 mmol). After 48 h, the reaction was completed acetone was removed under reduced pressure and the crude was dissolved in Ethyl acetate, washed with water and brine (2×) and finally dried over magnesium sulfate, filtrated and concentrated.

The crude (930 mg) was purified by flash chromatography with DCM/MeOH/NH$_4$OH 90/10/1. 354 mg of a nice yellow powder were isolated (yield=70%).

1H NMR (CDCl3): 1.25 (t, J=6.2 Hz, 3H), 1.35 (s, 9H), 2.12 (m, 2H), 2.35 (t, J=6.6 Hz, 2H), 4.12 (q, J=6.2 Hz, 2H), 4.34 (t, J=7.3 Hz, 2H), 7.21 (s, 1H), 7.45 (d, J=7.7 Hz, 2H), 8.03 (m, 4H), 8.31 (d, J=6.2 Hz, 2H). MS (ESI, +): 503 (M+1)

Compound 7c: Potassium salt of 4-{[1-(4-tert-butylphenyl)-3-pyridin-4-yl-1H-pyrazol-5-yl]amino}butanoic acid A solution of ester 7b (234 mg, 0.47 mmol) in methanol/water, (1:1, 10 mL) was heated under reflux for 8 h in presence of potassium carbonate (195 mg, 1.41 mmol). The mixture was then concentrated under reduced pressure, toluene was added and removed under reduced pressure. The crude thus obtained (398 mg) was analyzed (see below) and directly engaged in the next step.

1H NMR (DMSO): 1.34 (s, 9H), 1.82 (t, J=6.2 Hz, 2H), 2.01 (t, J=6.3 Hz, 2H), 4.55 (t, J=6.6 Hz, 2H), 5.75, s, 1H), 6.32 (s, 1H), 7.58 (s, 4H), 8.33 (d, J=5.1 Hz, 2H), 8.98 (d, J=5.5 Hz, 2H). MS (ESI, +): 379 (M+1)

Compound 7d: O-(tert-butyl)tyrosinamide

N-Fmoc-O-tert-butyl-tyrosine (3.27 g, 7.12 mmol) was dissolved in dioxane (15 mL). Ammonium hydrogenocarbonate (732 mg, 9.26 mmol), di-tert-butyl-dicarbonate (2.02 g, 9.26 mmol) and pyridine (0.4 mL) were added and the mixture was stirred under nitrogen atmosphere at room temperature for 12 h. It was then diluted with ethyl acetate and the organic phase was washed with brine (2×), 5% sulfuric acid (1×) and brine again. It was dried over magnesium sulfate and concentrated. The crude thus obtained (3.17 g) was dissolved in dichloromethane (50 mL) and diethylamine (10 mL). The mixture was stirred at room temperature for 12 h, concentrated under reduced pressure and purified by flash chromatography with DCM/MeOH/NH$_4$OH (95/5/1 then 90/10/1) to give 1.37 g of the desired compound (yield=81%).

$^1$H NMR (CDCl$_3$): 1.32 (s, 9H), 2.66 (dd, J=9.5 and 13.6 Hz, 1H), 3.20 (dd, J=3.7 and 13.9 Hz, 1H), 3.57 (dd, J=4.0 and 9.5 Hz, 1H), 5.40 (m, 1H), 6.93(d, J=7.0 Hz, 2H), 7.06 (m, 1H), 7.10 (d, J=7.3 Hz, 2H). MS (ESI, +): 237 (M+1)

Compound 7e: N-(4-{[1-(4-tert-butylphenyl)-3-pyridin-4-yl-1H-pyrazol-5-yl]amino}butanoyl)-O-(tert-butyl)tyrosinamide Compound 7c (170 mg, 0.45 mmol) was reacted with 1-ethyl-3-(3'-dimethylaminopropyl)carbodiimide hydrochloride (104 mg, 0.54 mmol), HOAT (73 mg, 0.54 mmol) and diisopropylamine (230 µl, 1.35 mmol) in dimethylformamide (6 mL). O-(tert-butyl)tyrosinamide 7d (118 mg, 0.50 mmol) was then added and the reaction mixture was stirred at room temperature under nitrogen atmosphere. After completion of the reaction (48 h), it was diluted with ethyl acetate and water. The two layers were separated and it appeared that the product was essentially in the aqueous phase. This latter was concentrated and injected on HPLC deltapack C18 column for purification using a gradient of water/acetonitrile from 95/5 to 40/60 in 60 min. 96 mg of pure compound was isolated after lyophilisation (yield=36%).

$^1$H NMR (CDCl$_3$): 1.25 (s, 9H), 1.35 (s, 9H), 2.20–2.43 (m, 4H), 2.90 (t, J=9.9 Hz, 1H), 3.18 (brd, J=10.6 Hz, 1H)) 4.27–4.52 (m, 7H), 6.20 (s, 1H), 6.84 (d, J=8.0 Hz, 2H), 7.15 (d, J=8.0 Hz, 2H), 7.50 (m, 4H), 8.18 (m, 2H), 8.29 (m, 1H), 8.53 (m, 1H). MS (ESI, +): 597 (M+1)

Compound 7: Compound 7e (89 mg, 0.15 mmol) was dissolved in dichloromethane and trifluoroacetic acid was added. The mixture was stirred overnight and concentrated to give 103 mg of a brown solid (quantitative yield).

1H NMR (DMSO): 0.82 (m, 2H), 1.33 (s, 9H), 2.13 (m, 2H), 2.60 (m, 1H), 2.86 (m, 1H), 4.19–4.38 (m, 3H), 5.81 (m, 1H), 6.32 (s, 1H), 6.63 (d, J=6.6 Hz, 2H), 7.00 (d, J=6.6 Hz, 2H), 7.01 (s, 1H), 7.45 (s, 1H), 7.58 (brs, 4H), 7.69 (m, 2H), 8.02 (d, J=8.4 Hz, 1H), 8.34 (d, J=5.1 Hz, 2H), 8.85 (d, J=5.1 Hz, 2H), 9.16 (s, 1H).

EXAMPLE 8

CHO Parental Cells Assay

The following compound 1-B was demonstrated to be hFSHR specific by testing it on untransfected CHO parental cells.

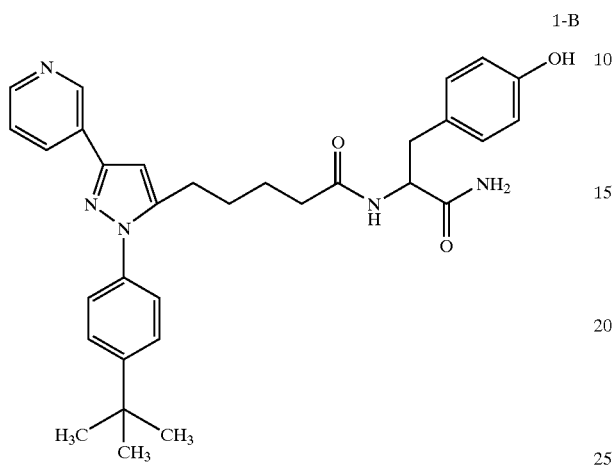

1-B

Briefly CHO parental cells were plated in 96 well packard view plates 5×10⁴ cells/well in serum containing media. After 20 hours the cells were confluent. The wells were washed with serum free assay medium (containing 0.1 mM MIX) and pre-incubated for 15 minutes in this medium. Compound 1 and forskolin (positive control) were added and the cells were incubated for an additional one hour. The cells were lysed and intracellular cAMP was measured using the Amersham direct one step cAMP-RIA kit according to the manufacturers directions. Compound 1 showed no response over background.

These cells were shown to have no response over background to stimulation with a $10^{-7}$ (M) dose of rhFSH in a previous experiment. In both experiments forskolin showed a five fold response over background.

EXAMPLE 9

FSH Assay Method

All compounds were stored in 96-well deepwell plates in DMSO at a nominal concentration of 10 mM (assuming perfect synthesis and yields). Compounds were screened for agonist activity at the FSH receptor using the recombinant FSH receptor stably transfected and expressed in Chinese Hamster Ovary Cells (CHO cells) essentially as described in the work by Kelton, et al. (Molecular and Cellular Endocrinology, 1992, 89, 141–151). Since the FSH receptor is known to act via a G-protein (Gs) to activate adenylyl cyclase and hence raise intracellular levels of cAMP the high throughput screening (HTS) assay used a gene reporter system consisting of the cAMP response element coupled upstream to the reporter gene which, in this case was the enzyme luciferase. Thus an agonist at the FSH receptor increases cAMP in the cell which results in activation of the CREB (cAMP) response element binding protein). This molecule interacts with the CRE element on the gene in the nucleus and results in increased transcription of the genes downstream of this element. The substrate for the enzyme (Packard Instrument Company 800 Research Parkway, Meriden, Conn. 06450, USA) was added to the cells after appropriate incubation with the compounds or FSH and the amount of luciferase expressed was measured by quantitating the luminescence produced by the enzyme using a TopCount scintillation/luminescence counter running in single photon counting mode. A compound which acted as an agonist at the receptor should produce light from the treated cells in proportion to its concentration within the incubation. Luminescence should be saturable at high concentrations of the compound.

EXAMPLE 10

HTS Primary Assay

The compounds, in deepwell plates (Master plates) as indicated above were loaded on the robotic deck along with the appropriate number of assay plates and daughter plates. A 10 μl aliquot from each master plate was transferred to the corresponding daughter plate and 90 μl of DME/F12 was added and mixed within each well. 20 μl was then removed from the daughter plate and dispensed into the assay plate. After addition of an aliquot of FSH (equivalent to an EC100 response for this hormone [Final concentration of 5c-11M]) to each of three wells on the plate, 80 ul of media (DME/$F^{12+}$ 2% serum) and 100 ul aliquot of cells (4×10⁵/ml in the same media) were added and the plate incubated at 37° C. for 3 hrs 30 min. At this time the plate was removed from the incubator and media in each well was aspirated and the cells adhering to the bottom of the plate washed with 300 ul PBS containing 1 mM $ca^{2+}$ and 1 mM $Mg^{2+}$. The PBS was aspirated and 100 ul PBS added to each well. 100 ul of Lucite (prepared as described by the manufacturer) was added to each well and the plate was shaken gently for 40 seconds prior to placement in the TopCount plate reader. After allowing 3.5 minutes for the plate to dark-adapt within the machine, the amount of luminescence generated was quantiated using Single Photon Counting mode. The data was transmitted electronically from the TopCount to the robot processing computer terminal and was renamed with an ID corresponding to the original master plate ID. Data was evaluated using an Excel macro and compounds showing activity comparable to that produced by an EC100 of FSH itself were further analyzed in the same assay at differing concentrations. LDR (log-dose-response) curves were generated for these compounds in CHO cells containing the FSH receptor and these curves were also compared with those in either cells expressing a different Gs linked receptor or in cells lacking any transfected receptor and these curves were also compared with those in either cells expressing a different Gs linked receptor or in cells lacking any transfected receptor.

Compounds which showed receptor specificity and activity at low concentrations were progressed to secondary assays which included dose-response curves in Y1 cells co-expressing the human FSH receptor or in isolated rat granulosa cells.

EXAMPLE 11

Secondary Assay; Rat Granulosa Cell Assay

A primary rat granulosa cell bioassay for follicle stimulating hormone (FSH) was used. Conversion of testosterone to estradiol in the presence of low nanomolar concentrations of FSH was detected using this assay. In this in vitro assay, conversion of androstendione to estrogen by granulosa cells in the presence of FSH was measured using a RIA.

Granulosa cell culture and FSH stimulation: Cells were plated at 5000, 8,000 and 20,000 cells/well/200 μl of GAB medium on poly-D-lysine coated 96-well tissue culture plates. Plates were incubated at 37° C. in a 5% CO/95% air incubator for 3 days. Cultures were washed prior to stimulation with FSH or LH. 50 μl of 4× concentrations of rhFSH, rhLH or forskolin was added to the cultures. To define the range of the dose response curve the rhFSH was diluted so that the final concentration on the cells was between $10^{-7}$ to $10^{-15}$ (M) with three doses per log at 1, 2 and 5. Forskolin was diluted so that the final concentration on the cells was 1 μM. Cells were incubated @ 37° C. in 5% $CO_2$. Three days later, cell supernatants were collected and diluted 1:100 in GAB medium for measurement of estradiol by RIA. The RIA was performed according to manufacturer directions except that an estradiol standard was prepared in absolute ethanol at 100 ng/ml and then further diluted in GAB medium, instead of kit buffer. The concentration of hormone was plotted on the X-axis against the amount of estradiol produced by the cells on the Y-axis using Origin graphics software.

The invention has been described in detail with reference to preferred embodiments thereof. However, it will be appreciated that those skilled in the art, upon consideration of this disclosure, may make modifications and improvements within the spirit and scope of the invention.

What is claimed is:

1. A compound of the following Formula I;

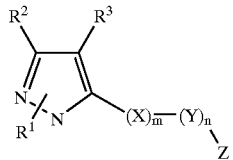

I wherein $R^1$ is optionally substituted alkyl or para substituted phenyl;

$R^2$ is pyridyl, quinoline or isoquinoline;

$R^3$ is hydrogen;

X is optionally substituted alkylene; optionally substituted alkenylene; optionally substituted alkynylene; optionally alicyclic, optionally substituted carbocyclic aryl;

Y is optionally substituted amino; optionally substituted methylene; carbonyl; or sulfonyl;

Z is an alkylamine substituted with a phenolic group on the alkyl chain; an amino acid selected from the group consisting of tyrosine, homo-tyrosine, β-homo-tyrosine, meta-tyrosine, threonine, serine, 4-hydroxymethyl-phenylalanine, 4-amino-phenylalanine, 4-acetyl-amino-phenylalanine, and 4-hydroxy-α-phenylglycine; m is 0 or 1; n is 0 or 1; and pharmaceutically acceptable salts thereof.

2. A compound of claim 1 wherein the compound is of the following Formula IA:

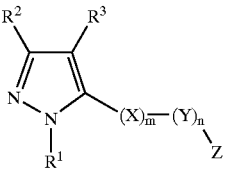

IA wherein $R^1$ is optionally substituted alkyl or para substituted phenyl;

$R^2$ is pyridyl, quinoline or isoquinoline;

$R^3$ is hydrogen;

X is optionally substituted alkylene; optionally substituted alkenylene; optionally substituted alkynylene; optionally alicyclic, optionally substituted carbocyclic aryl;

Y is optionally substituted amino; optionally substituted methylene; carbonyl; or sulfonyl;

Z is an alkylamine substituted with a phenolic group on the alkyl chain; an amino acid selected from the group consisting of tyrosine, homo-tyrosine, β-homo-tyrosine, meta-tyrosine, threonine, serine, 4-hydroxymethyl-phenylalanine, 4-amino-phenylalanine, 4-acetyl-amino-phenylalanine, and 4-hydroxy-α-phenylglycine; m is 0 or 1; n is 0 or 1; and pharmaceutically acceptable salts thereof.

3. A compound of claim 1 wherein $R^1$ is optionally substituted alkyl.

4. A compound of claim 1 wherein $R^1$ is arylalkyl.

5. A compound of claim 1 wherein $R^1$ is para substituted phenyl.

6. A compound of claim 1 wherein $R^1$ is phenyl substituted by alkyl in the 4-position.

7. A compound of claim 1 wherein $R^2$ is pyridyl.

8. A compound of claim 1 wherein $R^2$ is quinoline.

9. A compound of claim 1 wherein $R^2$ is isoquinoline.

10. A compound of claim 1 wherein X is an optionally substituted alkylene group.

11. A compound of claim 1 wherein X is an optionally substituted carbocyclic aryl.

12. A compound of claim 1 wherein X is —$CH_2CH_2CH_2CH_2$— or —$CH_2CH_2CH_2CH_2CH_2$—.

13. A compound of claim 1 wherein the compound is selected from the group consisting of:

N-{5-[1-(4-tert-butylphenyl)-3-pyridin-2-yl-1H-pyrazol-5-yl]pentanoyl}tyrosinamide;

N-{5-[1-(4-tert-butylphenyl)-3-pyridin-3-yl-1H-pyrazol-5-yl]pentanoyl}tyrosinamide;

N-{5-[1-(4-tert-butylphenyl)-5-pyridin-3-yl-1H-pyrazol-3-yl]pentanoyl}tyrosinamide;

N-{5-[1-(4-tert-butylphenyl)-3-pyridin-4-yl-1H-pyrazol-5-yl]pentanoyl}tyrosinamide;

N-{5-[1-(4-tert-butylphenyl)-5-pyridin-4-yl-1H-pyrazol-3-yl]pentanoyl}tyrosinamide;

N-{5-[1-(4-tert-butylphenyl)-3-pyridin-3-yl-1H-pyrazol-5-yl]pentanoyl}-N,N-dimethyltyrosinamide;

N-3-[1-(4-tert-butylphenyl)-5-pyridin-3-yl-1H-pyrazol-3-yl]propanoyl)tyrosinamide;

N-3-[1-(4-tert-butylphenyl)-3-pyridin-5-yl-1H-pyrazol-3-yl]propanoyl)tyrosinamide;

N-[4-(1-butyl-isoquinolin-3-yl-1H-pyrazol-5-yl)benzoyl]tyrosinamide;

N-{5-[1-(4-isopropylphenyl)-3-pyridin-3-yl-1H-pyrazol-5-yl]pentanoyl}tyrosinamide;

N-{6-[1-(4-isopropylphenyl)-3-pyridin-2-yl-1H-pyrazol-5-yl]hexanoyl}tyrosinamide;

N-{6-[1-(4-tert-butylphenyl)-3-pyridin-2-yl-1H-pyrazol-5-yl]hexanoyl}-3-hydroxyphenylalaninamide;

N-[5-(1-butyl-isoquinolin-3-yl-1H-pyrazol-5-yl)pentanoyl]tyrosinamide;

N-{6-[1-(4-tert-butylphenyl)-3-pyridin-2-yl-1H-pyrazol-5-yl]hexanoyl}serinamide;

N-{6-[1-(4-iso-propylphenyl)-3-pyridin-2-yl-1H-pyrazol-5-yl]hexanoyl}serinamide;

N-{6-[1-(4-iso-propylphenyl)-3-pyridin-2-yl-1H-pyrazol-5-yl]hexanoyl}threonamide;

N-{5-[1-(4-isopropylphenyl)-3-pyridin-2-yl-1H-pyrazol-5-yl]pentanoyl}tyrosinamide;

6-[1-(4-tert-butylphenyl)-3-pyridin-2-yl-1H-pyrazol-5-yl]-N-[2-4-hydroxyphenyl)ethyl]hexanamide;

N-{6-[1-(4-tert-butylphenyl)-3-pyridin-2-yl-1H-pyrazol-5-yl]hexanoyl}tyrosinamide;

N-{5-[1-(4-tert-butylphenyl)-3-isoquinolin-3-yl-1H-pyrazol-5-yl]pentanoyl}tyrosinamide;

N-{6-[1-(4-tert-butylphenyl)-3-isoquinolin-3-yl-1H-pyrazol-5-yl]hexanoyl}tyrosinamide;

N-{6-[1-(4-tert-butylphenyl)-3-pyridin-2-yl-1H-pyrazol-5-yl]hexanoyl}-N-methyltyrosinamide;

N-{5-[1-(4-tert-butylphenyl)-3-isoquinolin-3-yl-1H-pyrazol-5-yl]pentanoyl}tyrosinamide;

N-{6-[1-(4-tert-butylphenyl)-3-pyridin-2-yl-1H-pyrazol-5-yl]hexanoyl}-4-(hydroxymethyl)phenylalaninamide;

4-amino-N-{6-[1-(4-tert-butylphenyl)-3-pyridin-2-yl-1H-pyrazol-5-yl]hexanoyl}phenylalaninamide;

4-(acetylamino)-N-{6-[1-(4-tert-butylphenyl)-3-pyridin-2-yl-1H-pyrazol-5-yl]hexanoyl}phenylalaninamide;

4-(aminocarbonyl)-N-{6-[1-(4-tert-butylphenyl)-3-pyridin-2-yl-1H-pyrazol-5-yl]hexanoyl}phenylalaninamide;

N-butyl-N-{6-[1-(4-tert-butylphenyl)-3-pyridin-2-yl-1H-pyrazol-5-yl]hexanoyl}tyrosinamide;

N-{6-[1-(4-tert-butylphenyl)-3-pyridin-2-yl-1H-pyrazol-5-yl]hexanoyl}threonamide;

N-[2-amino-1-(4-hydroxyphenyl)-2-oxoethyl]-6-[1-(4-tert-butylphenyl)-3-pyridin-2-yl-1H-pyrazol-5-yl]hexanamide;

N-[2-amino-1-(4-hydroxyphenyl)-2-oxoethyl]-4-[1-(4-tert-butylphenyl)-3-pyridin-2-yl-1H-pyrazol-5-yl]benzamide;

4-[1-(4-tert-butylphenyl)-3-pyridin-2-yl-1H-pyrazol-5-yl]-N-[2-(4-hydroxyphenyl)ethyl]benzamide;

N-{3-[1-(4-tert-butylphenyl)-3-isoquinolin-3-yl-1H-pyrazol-5-yl]benzoyl}tyrosinamide;

N-{5-[1-(4-tert-butylphenyl)-3-pyridin-4-yl-1H-pyrazol-5-yl]pentanoyl}tyrosinamide;

N-{3-[1-(4-tert-butylphenyl)-3-pyridin-3-yl-1H-pyrazol-5-yl]benzoyl}tyrosinamide;

N-{3-[1-(4-tert-butylphenyl)-3-isoquinolin-3-yl-1H-pyrazol-5-yl]benzoyl}tyrosinamide;

N-{3-[1-(4-tert-butylphenyl)-3-quinolin-3-yl-1H-pyrazol-5-yl]benzoyl}tyrosinamide;

N-{3-[3-isoquinolin-3-yl-1-(4-propylphenyl)-1H-pyrazol-5-yl]benzoyl}tyrosinamide;

N-{3-[1-(4-tert-butylphenyl)-3-pyridin-3-yl-1H-pyrazol-5-yl]benzoyl}tyrosinamide;

N-{4-[1-(4-tert-butylphenyl)-3-pyridin-3-yl-1H-pyrazol-5-yl]benzoyl}tyrosinamide;

N-{5-[1-(4-tert-butylphenyl)-3-pyridin-4-yl-1H-pyrazol-5-yl]pentanoyl}tyrosinamide;

N-{3-[1-(4-tert-butylphenyl)-3-pyridin-4-yl-1H-pyrazol-5-yl]benzoyl}tyrosinamide;

N-{5-[1-(4-tert-butylphenyl)-3-pyridin-3-yl-1H-pyrazol-5-yl]pentanoyl}tyrosinamide;

N-[3-(1-butyl-3-isoquinolin-3-yl-1H-pyrazol-5-yl)benzoyl]tyrosinamide;

N-{3-[1-(4-tert-butylphenyl)-3-pyridin-4-yl-1H-pyrazol-5-yl]propyl}tyrosinamide;

N-acetyl-N-{3-[1-(4-tert-butylphenyl)-3-pyridin-4-yl-1H-pyrazol-5-yl]propyl}tyrosinamide;

N-[1-(aminocarbonyl)-3-(4-hydroxyphenyl)propyl]-5-[1-(4-tert-butylphenyl)-3-pyridin-2-yl-1H-pyrazol-5-yl]pentanamide;

N-{5-[1-(4-tert-butylphenyl)-3-quinolin-3-yl-1H-pyrazol-5-yl]pentanoyl}tyrosinamide;

N-[5-(1-butyl-3-quinolin-6-yl-1H-pyrazol-5-yl)pentanoyl]tyrosinamide;

N-{5-[1-(4-tert-butylphenyl)-3-quinolin-6-yl-1H-pyrazol-5-yl]pentanoyl}tyrosinamide;

N-{5-[1-(4-tert-butylphenyl)-3-quinolin-6-yl-1H-pyrazol-5-yl]pentanoyl}tyrosinamide; or an optical isomer, racemate or tautomer of any one thereof or a pharmaceutically acceptable salt of any one thereof.

14. A compound that is:

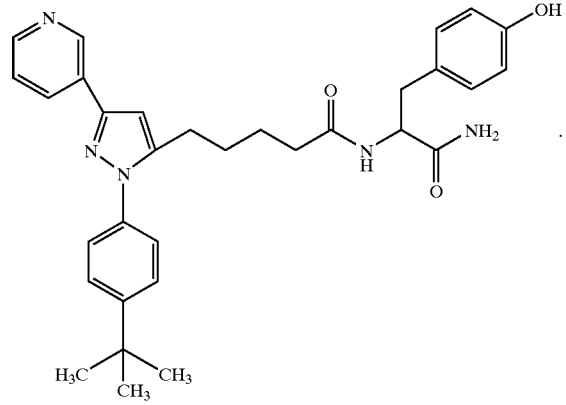

15. A pharmaceutical composition comprising a pharmaceutically acceptable carrier and one or more compounds as in claim 1 or 14.

16. A pharmaceutical composition comprising one or more compounds as in claim 1 or 14 wherein the composition is in an oral dosage form.

17. A compound of claim 1, wherein Z is tyrosine.

18. A compound of claim 1, wherein Z is selected from —NHCH(CH$_2$C$_6$H$_4$OH)C(=O)NH$_2$, —NH{CH$_2$C$_6$H$_3$—(N=C—NH—)}C(=O)NH$_2$, and —NH{CH$_2$C$_6$H$_3$—(N=N—NH—)}C(=O)NH$_2$.

19. A compound of claim 1, wherein Z is —NHCH(CH$_2$C$_6$H$_4$OH)C(O)NH$_2$.

* * * * *

UNITED STATES PATENT AND TRADEMARK OFFICE
CERTIFICATE OF CORRECTION

PATENT NO. : 6,914,069 B2  
DATED : July 5, 2005  
INVENTOR(S) : H. Shroff et al.

It is certified that error appears in the above-identified patent and that said Letters Patent is hereby corrected as shown below:

Column 8,
Line 26, please correct "or 2 A is" to -- or 2; A is --.

Column 12,
Line 3, please correct "ethyltyrosinamide" to -- ethyl]tyrosinamide --.

Column 16,
Compound 1, please correct

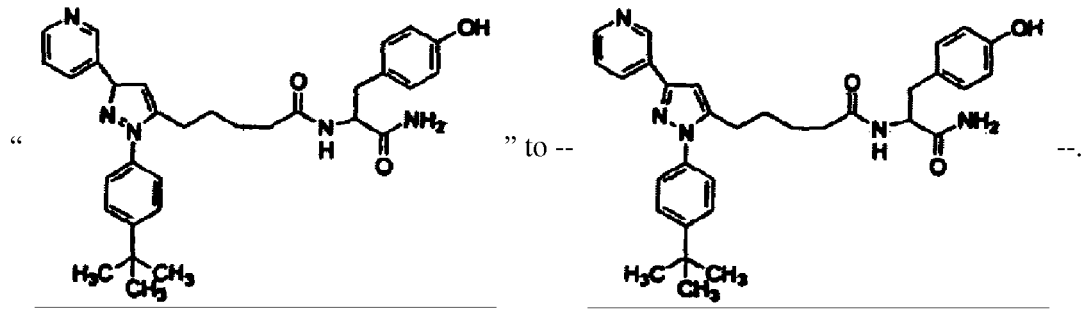

Column 21,
Compound 2, please correct

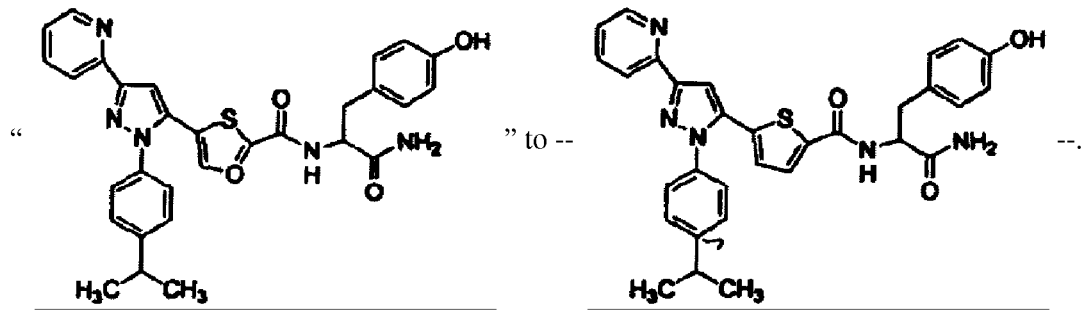

Column 29,
Line 38, please correct "tyro sine" to -- tyrosine --.

Column 37,
Lines and 52, please correct "a 1 bottle" to -- a 1L bottle --.

UNITED STATES PATENT AND TRADEMARK OFFICE
CERTIFICATE OF CORRECTION

PATENT NO. : 6,914,069 B2
DATED : July 5, 2005
INVENTOR(S) : H. Shroff et al.

It is certified that error appears in the above-identified patent and that said Letters Patent is hereby corrected as shown below:

Column 38,
Line 55, please correct

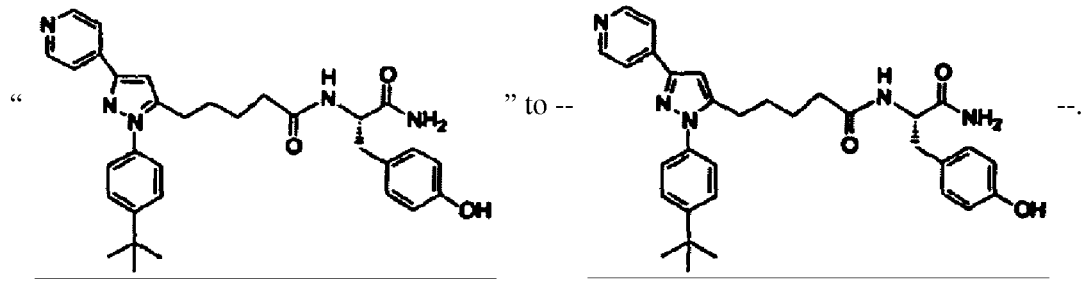

Column 39,
Line 21, please correct "4-yl-]-H-" to -- 4-yl-1H- --.

Column 41,
Line 23, please correct "1H-5-yl]" to -- 1H-pyrazol-5-yl] --.

Column 43,
Line 20, please correct

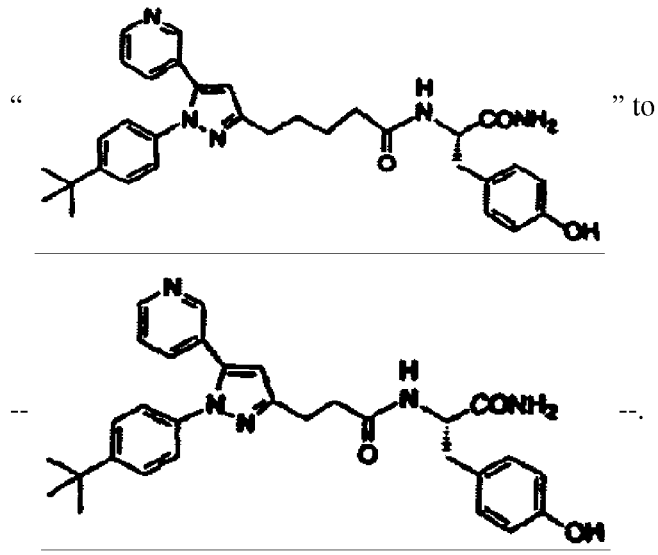

UNITED STATES PATENT AND TRADEMARK OFFICE
CERTIFICATE OF CORRECTION

PATENT NO. : 6,914,069 B2
DATED : July 5, 2005
INVENTOR(S) : H. Shroff et al.

It is certified that error appears in the above-identified patent and that said Letters Patent is hereby corrected as shown below:

Column 43 (cont'd),
Line 35, please correct

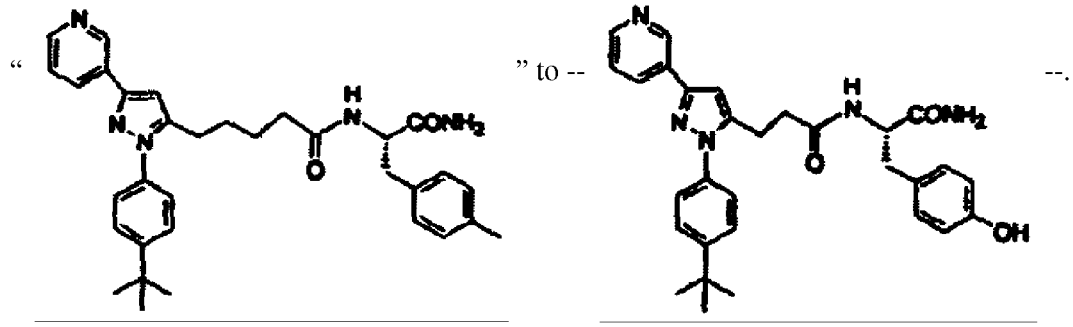

Column 44,
Line 27, please correct "$H_2Cr_2O_7$" to -- $H_2Cr_2O_7$ --.

Column 45,
Line 1, please correct "J 8.4 Hz," to -- J = 8.4 Hz, --.
Line 3, please correct "3.34" to -- 4.34 --.

Column 50,
Lines 51-52, please correct "pyridin-5-yl-1H-pyrazol-3-yl]" to
-- pyridin-3-yl-1H-pyrazol-5-yl] --.
Line 53, please correct "butyl-isoquinolin-" to -- butyl-3-isoquinolin- --.

Column 51,
Lines 46, 50 and 59, please correct "4-tert-butylphenyl" to -- 4-tert-butylbenzyl --.

UNITED STATES PATENT AND TRADEMARK OFFICE
CERTIFICATE OF CORRECTION

PATENT NO. : 6,914,069 B2
DATED : July 5, 2005
INVENTOR(S) : H. Shroff et al.

It is certified that error appears in the above-identified patent and that said Letters Patent is hereby corrected as shown below:

Column 52,
Lines 1, 3 and 22, please correct "4-tert-butylphenyl" to -- 4-tert-butylbenzyl --.

Signed and Sealed this

First Day of November, 2005

JON W. DUDAS
*Director of the United States Patent and Trademark Office*